(12) United States Patent
Chakrabarti et al.

(10) Patent No.: US 7,772,383 B2
(45) Date of Patent: Aug. 10, 2010

(54) CHEMICAL PCR: COMPOSITIONS FOR ENHANCING POLYNUCLEOTIDE AMPLIFICATION REACTIONS

(75) Inventors: Raj Chakrabarti, New York, NY (US); Clarence Schutt, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 596 days.

(21) Appl. No.: 10/792,404

(22) Filed: Mar. 3, 2004

(65) Prior Publication Data

US 2005/0042627 A1 Feb. 24, 2005

Related U.S. Application Data

(63) Continuation-in-part of application No. 10/056,917, filed on Jan. 25, 2002, now Pat. No. 6,494,368.

(60) Provisional application No. 60/451,642, filed on Mar. 4, 2003, provisional application No. 60/451,650, filed on Mar. 4, 2003.

(51) Int. Cl.
*C07H 19/00* (2006.01)
*C12P 19/34* (2006.01)

(52) U.S. Cl. ..................... 536/22.1; 435/91.2

(58) Field of Classification Search ........................ None
See application file for complete search history.

(56) References Cited

U.S. PATENT DOCUMENTS

| | | | |
|---|---|---|---|
| 5,432,065 A * | 7/1995 | Fuller | 435/91.1 |
| 5,545,539 A | 8/1996 | Miller | |
| 5,846,716 A | 12/1998 | Miller | |
| 6,114,150 A | 9/2000 | Weissman et al. | |
| 6,183,998 B1 * | 2/2001 | Ivanov et al. | 435/91.2 |
| 6,261,773 B1 | 7/2001 | Segawa et al. | |
| 6,300,075 B1 | 10/2001 | Preston et al. | |
| 6,410,725 B1 * | 6/2002 | Scholl et al. | 536/25.42 |
| 6,949,368 B2 * | 9/2005 | Chakrabarti et al. | 435/91.2 |
| 6,962,780 B2 * | 11/2005 | Nakayama et al. | 435/6 |
| 2006/0141491 A1 * | 6/2006 | Chakrabarti et al. | 435/6 |

OTHER PUBLICATIONS

Chakrabarti et al., The enhancement of PCR amplification by low molecular-weight sulfones, Gene 274 (2001) 293-298.*
Chakrabarti et al., The enhancement of PCR amplification by low molecular-weight amides., 2001 Nucleic Acids Research, vol. 29, No. 11, pp. 2377-2381.*
Brodbelt, Analytical Applications of Ion-Molecule Reactions, Mass Spectrometry Reviews, 1997, 16, 91-110.*
Dhe-Paganon et al., Crystal Structure of the HNF4_Ligand Binding Domain in Complex with Endogenous Fatty Acid Ligand, The Journal of Biological Chemistry, vol. 277, No. 41, Issue of Oct. 11, 2002, pp. 37973-37976, 2002.*
Karim et al., Convenient genotyping of six myostatin mutations causing double-muscling in cattle using a multiplex oligonucleotide ligation assay, Animal Genetics, 2000, 31, 396-399.*
McGraw-Hill's Encylcopedia of Science & Techonology Online, entry for "Polyol", 2008, obtained at: http://www.accessscience.com/content.aspx?id=535850.*
Chakrabarti, PCR Enhanment by Organic Solvents, Dissertation, Princeton University, Jun. 2002, lead pages and pp. 120-134 via ProQuest Information and Learning.*
Mudd Library Home Page, Princeton University, 2009, p. 1, via: http://www.princeton.edu/mudd.*
Roux, 1995 in Dieffenbach & Dvesksler eds., PCR Primer-A Laboratory Manual, Cold Spring Harbor Laboratory Press, Cold Spring Harbor, NY, pp. 55-66.
Newton & Graham, PCR, 1994, Bios Scientific, Oxford.
Varadaraj & Skinner, Gene 140, 1-5, 1994.
McDowell et al., Nucl. Acids Res. 26, 3340-3347, 1998.
Winship, Nucl. Acids Res. 17, 1266, 1989.
Smith et al., Amplifications 5, 16-17, 1990.
Wiessensteiner & Lanchbury, BioTechniques 21, 1102-1108, 1996.

* cited by examiner

*Primary Examiner*—Mark Staples
(74) *Attorney, Agent, or Firm*—Porzio, Bromberg & Newman, P.C.

(57) ABSTRACT

A composition for performing a polynucleotide amplification reaction at low temperature, including a polynucleotide amplification reaction mixture into which is incorporated a sufficiently high concentration of a low molecular weight compound selected from the group consisting of amides, sulfones, sulfoxides and diols, to accomplish the amplification at the low temperature.

In another embodiment, a composition for enhancing a polynucleotide amplification reaction, including a polynucleotide amplification reaction mixture into which is incorporated a low molecular weight diol in an amount effective to enhance the polynucleotide amplification.

17 Claims, 16 Drawing Sheets

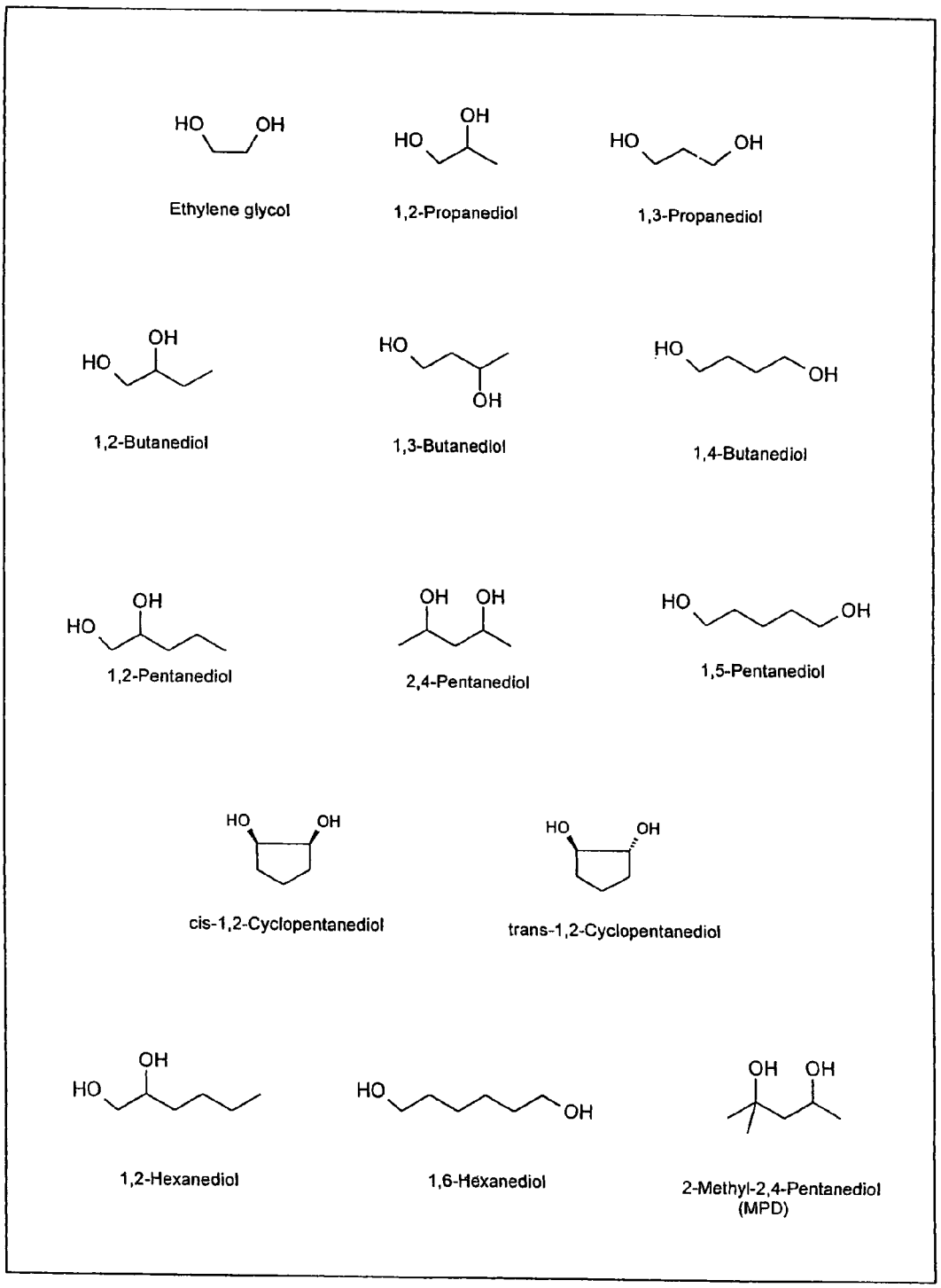
Figure 1  Structures of the low molecualr weight diols tested. Common names used are included in parentheses.

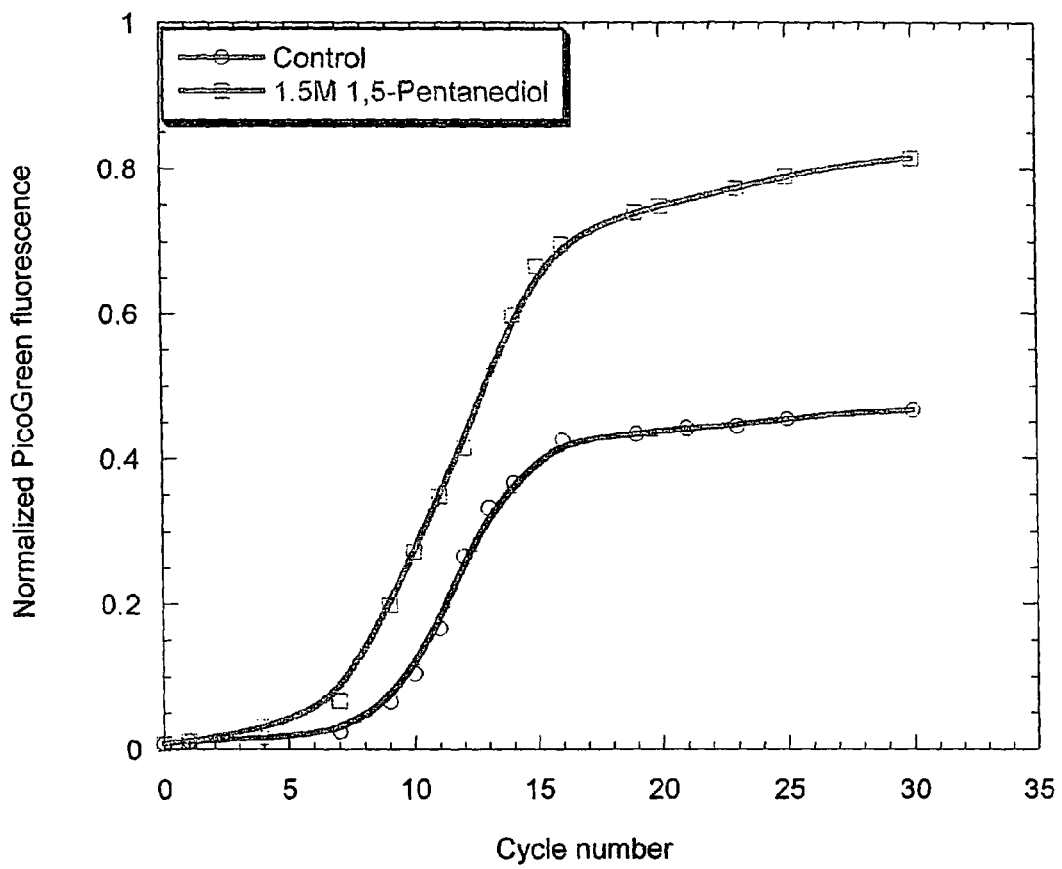

Figure 2. Real-time PCR amplification of c-jun in the absence of cosolvent and in the presence of 1.5M 1,5-pentanediol, under 80 / 50 / 53 °C cycling conditions. PicoGreen fluorescence is directly proportional to concentration of duplex DNA. Note:
1) Multiplicative rate of amplification is greater for control than for 1,5-pentanediol reaction, suggesting that lower melting templates are amplifying in the control reaction.
2) Control and 1,5-pentanediol reactions plateau at the same cycle, but the maximal control amplification is significantly lower. This suggests that plateau occurs due to primer depletion and that short, nonspecific background templates, instead of the desired c-jun template, are amplifying in the control.

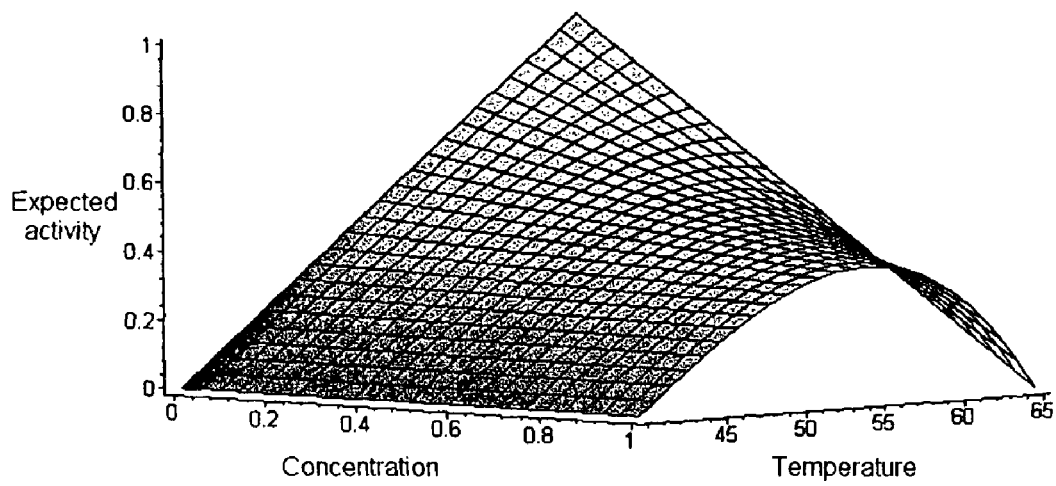

Figure 3  Representative plot of expected Taq polymerase activity versus cosolvent concentration and temperature. Actual activity surfaces may possess multiple maxima, and may exhibit activation above control activity levels. Finding efficient empirical methods for searching surfaces of this sort will constitute a critical component of chemical PCR optimization. The contributions of duplex DNA melting, DNA secondary structure dissociation, and polymerase thermostability to solvent-cycling space are simpler to map since the relevant conformational changes can be described conveniently by two state thermodynamic parameters

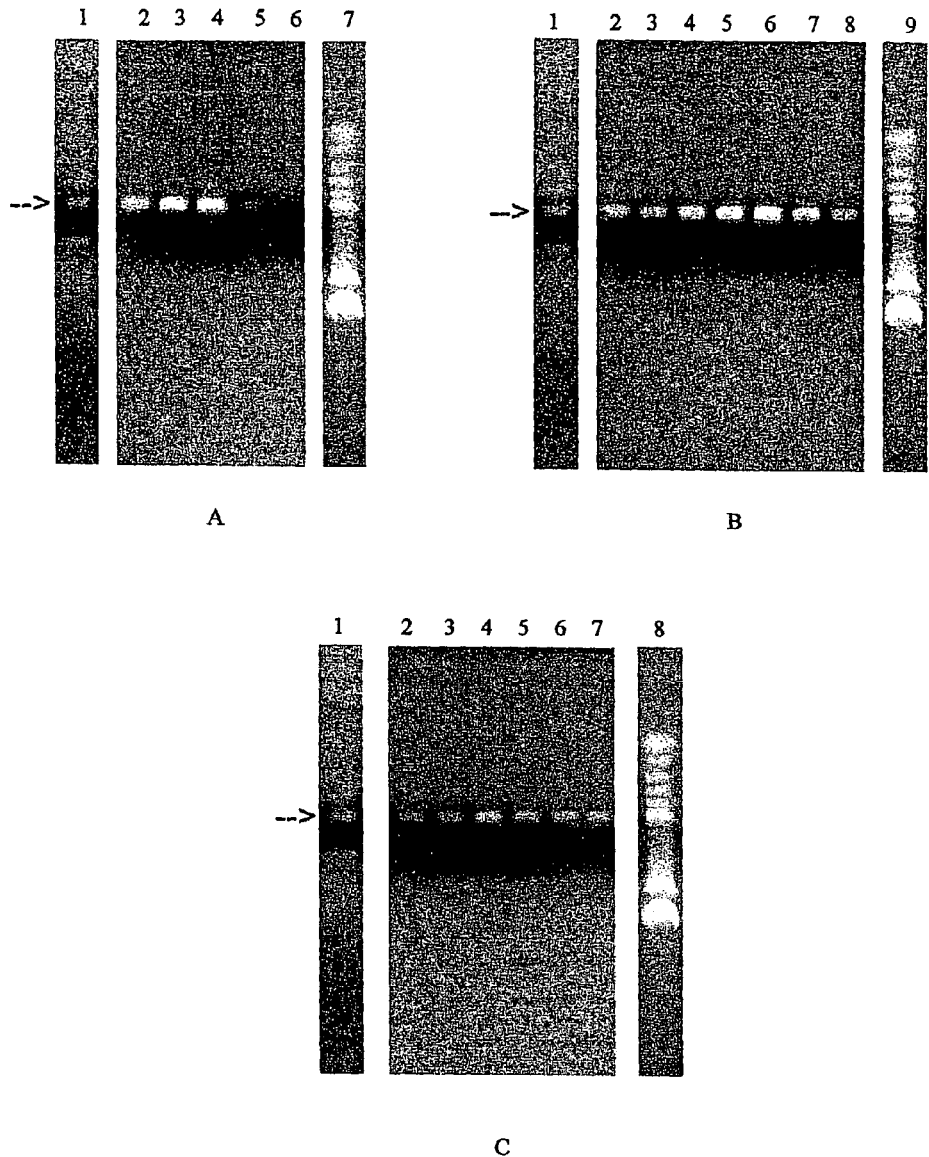

Figure 4  Enhancement of PCR amplification of GTP cDNA (660 bp) by 1,2-butanediol, 1,2-propanediol and glycerol (95°C denaturing). A. 1,2-Butanediol (54°C annealing). Lane 1: Control, Lane 2: 0.1M, Lane 3: 0.3M, Lane 4: 0.5M, Lane 5: 0.7M, Lane 6: 0.9M, Lane 7: 100 bp DNA ladder. B. 1,2-Propanediol (58°C annealing). Lane 1: Control, Lane 2: 0.3M, Lane 3: 0.5M, Lane 4: 0.9M, Lane 5: 1.1M, Lane 6: 1.4M, Lane 7: 1.6M, Lane 8: 1.8M, Lane 9: 100 bp DNA ladder. C. Glycerol (54°C annealing). Lane 1: Control, Lane 2: 0.1M, Lane 3: 0.3M, Lane 4: 0.5M, Lane 5: 0.7M, Lane 6: 0.9M, Lane 7: 1.1M, Lane 8: 100 bp DNA ladder. Arrow designates 660 bp.

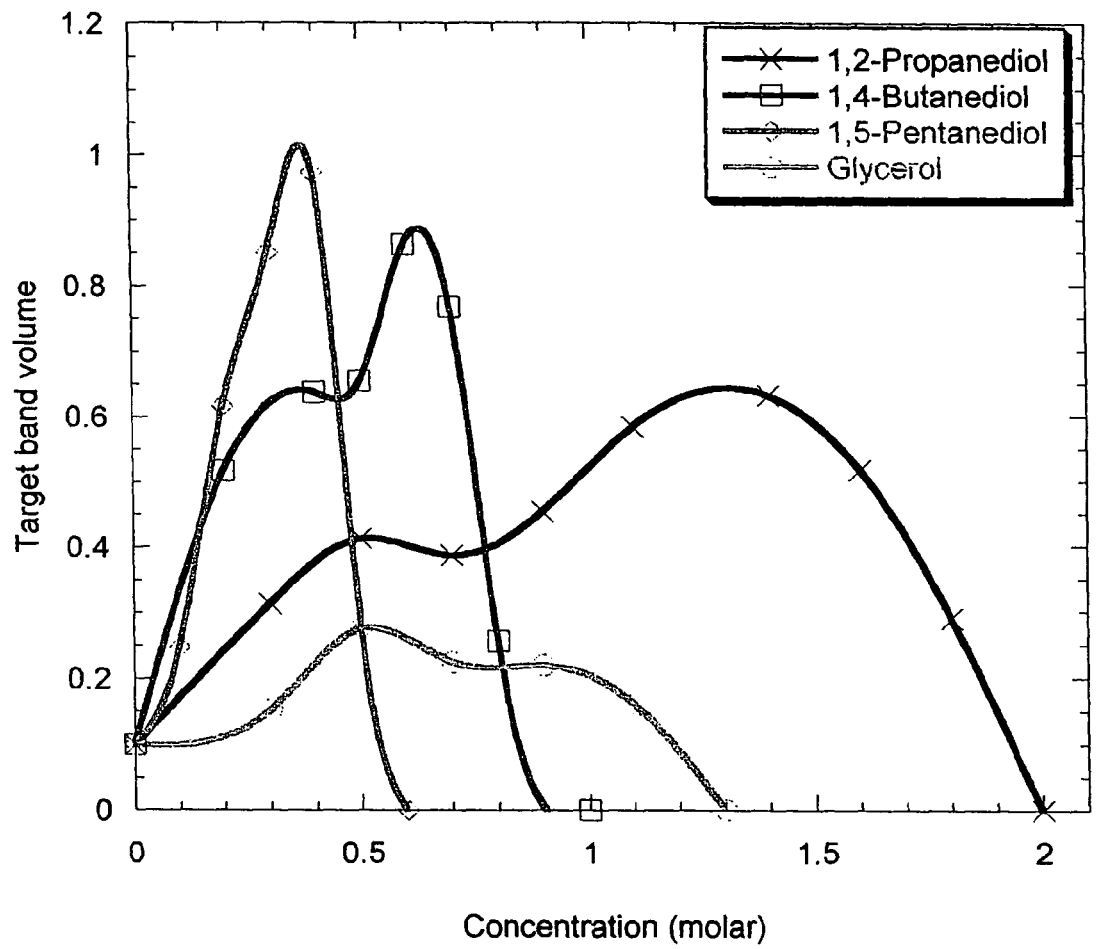
Figure 5  Variation of GTP amplification with concentration of selected diols and glycerol (standard). Target band volume is normalized to the potency of 1,5-pentanediol. Interpolation was carried out by fitting cubic splines to the data.

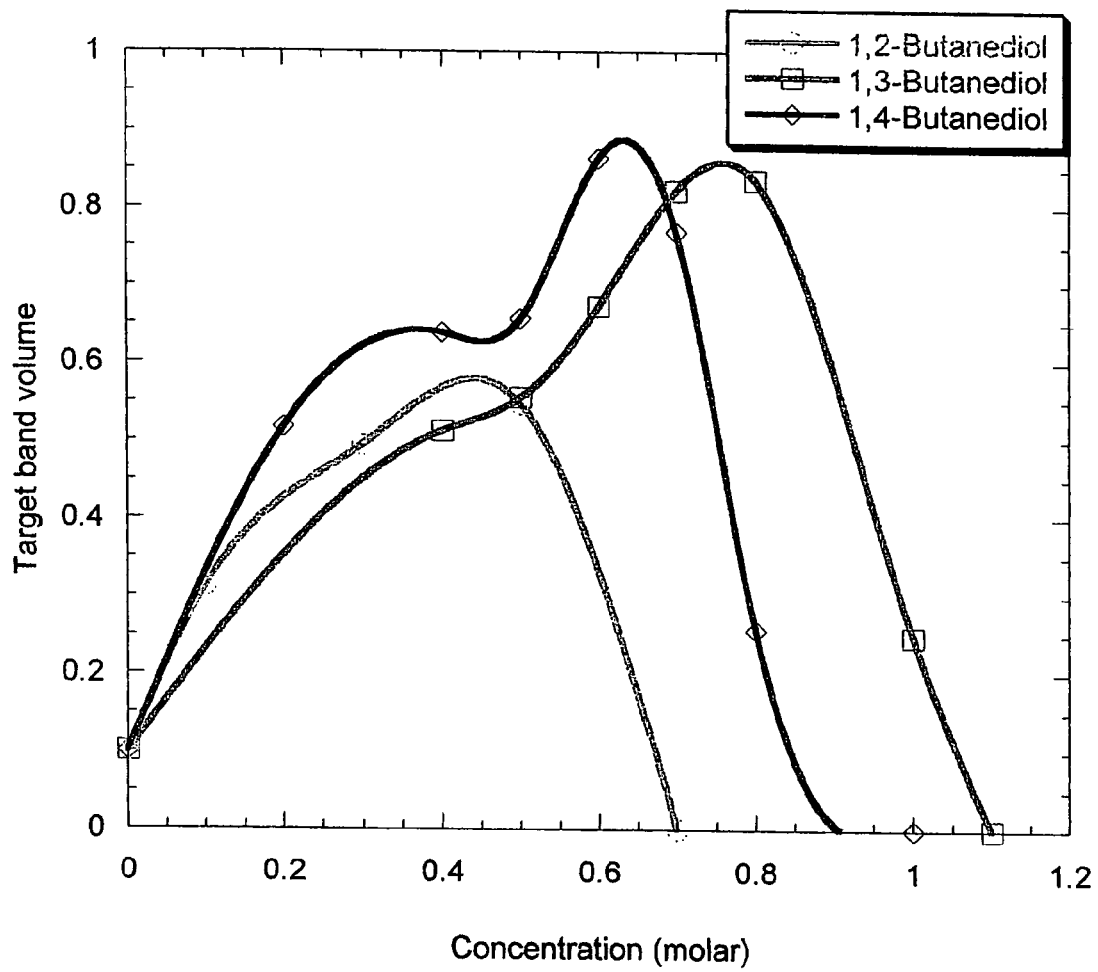
Figure 6. Variation of GTP amplification with concentration of butanediols. Target band volume is normalized to the potency of 1,5-pentanediol. Interpolation was carried out by fitting cubic splines to the data.

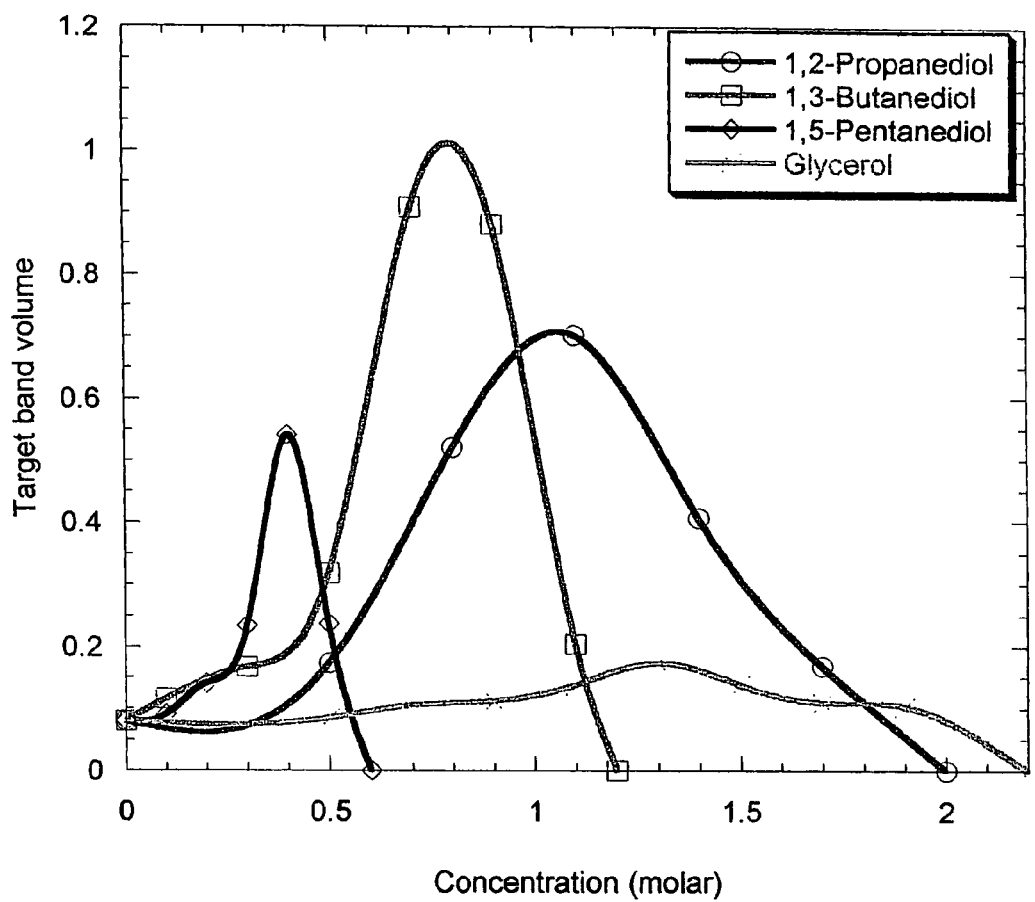
Figure 7. Variation of PSM amplification with concentration of selected diols and glycerol (standard). Target band volume is normalized to the potency of 1,3-butanediol. Interpolation was carried out by fitting cubic splines to the data.

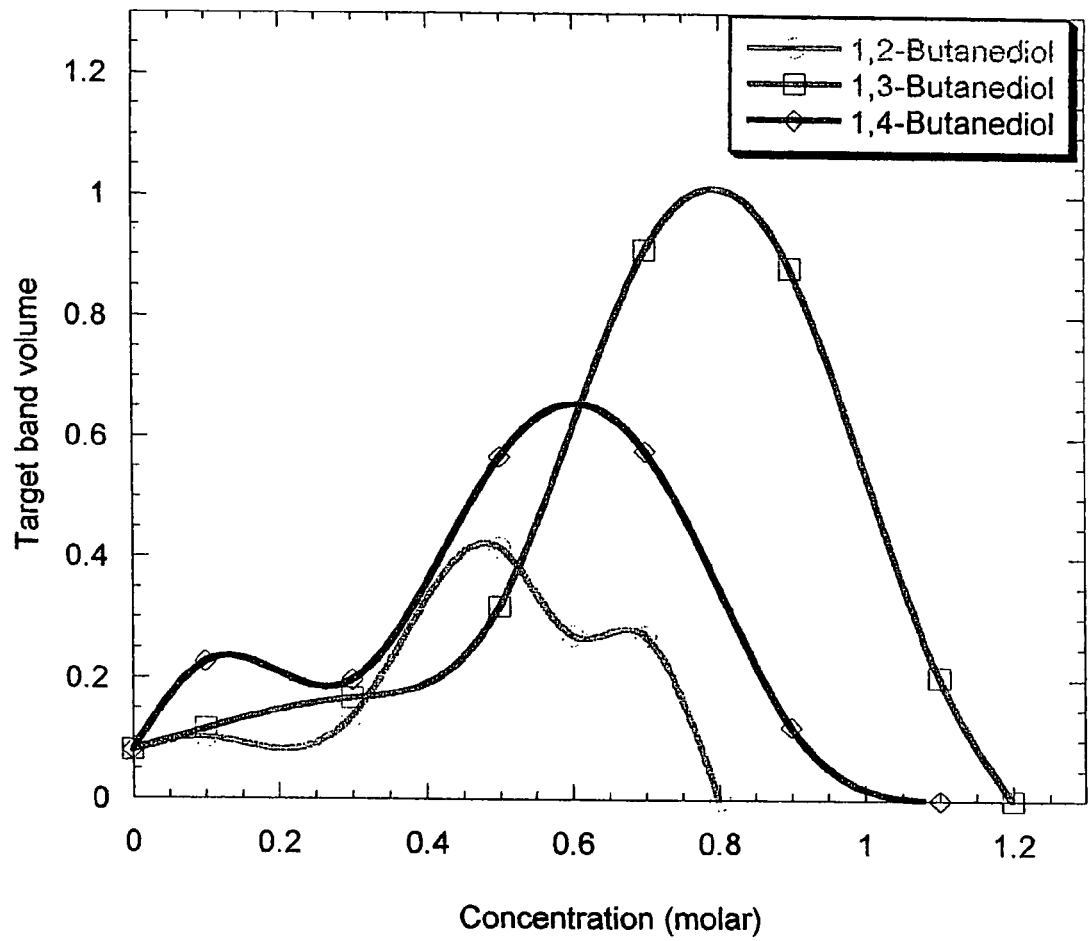
Figure 8   Variation of PSM amplification with concentration of butanediols. Target band volume is normalized to the potency of 1,3-butanediol. Interpolation was carried out by fitting cubic splines to the data.

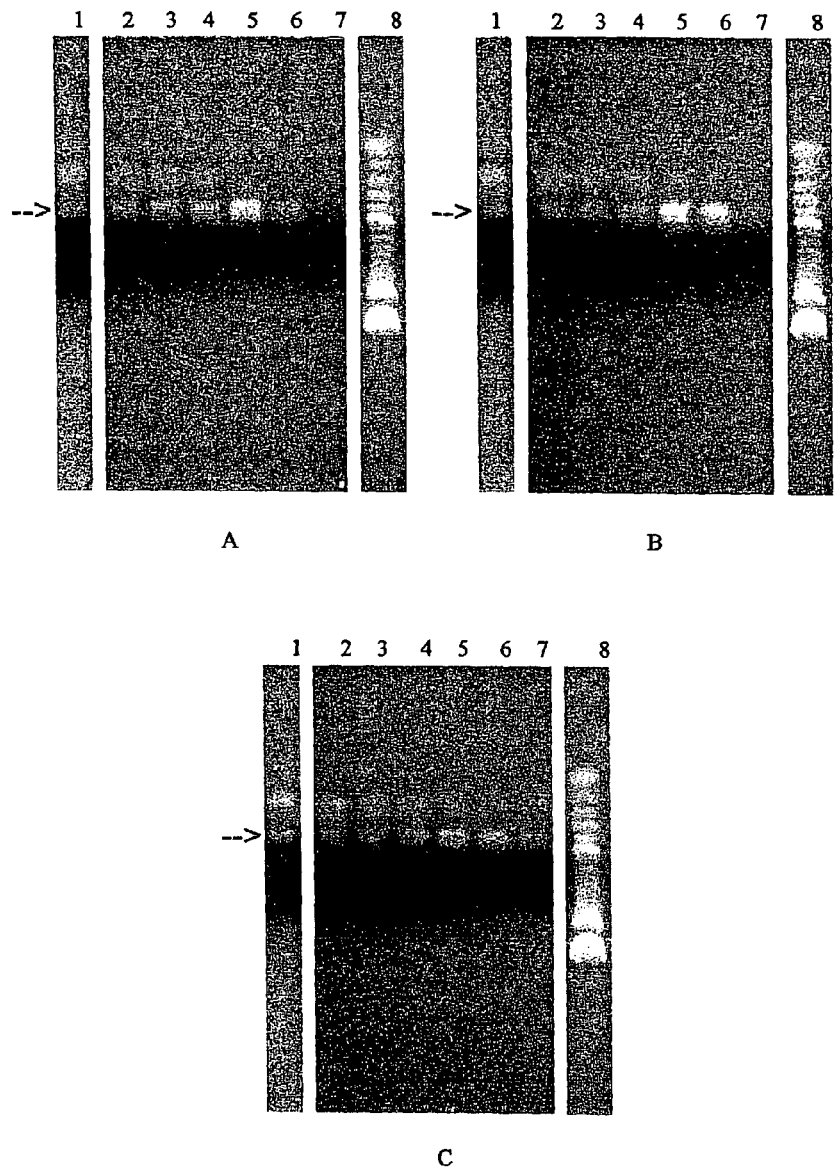

Figure 9 Enhancement of PCR amplification of PSM cDNA (511 bp segment) by 1,5-pentanediol, 1,3-butanediol and glycerol (95°C denaturing). A. 1,5-Pentanediol (52°C annealing). Lane 1: Control, Lane 2: 0.1M, Lane 3: 0.2M, Lane 4: 0.3M, Lane 5: 0.4M, Lane 6: 0.5M, Lane 7: 0.6M, Lane 8: 100 bp DNA ladder. B. 1,3-Butanediol (50°C annealing). Lane 1: Control, Lane 2: 0.1M, Lane 3: 0.3M, Lane 4: 0.5M, Lane 5: 0.7M, Lane 6: 0.9M, Lane 7: 1.1M, Lane 8: 100 bp DNA ladder. C. Glycerol (52°C annealing). Lane 1: Control, Lane 2: 0.7M, Lane 3: 0.9M, Lane 4: 1.1M, Lane 5: 1.3M, Lane 6: 1.5M, Lane 7: 1.9M, Lane 8: 100 bp DNA ladder. Arrow designates 511 bp.

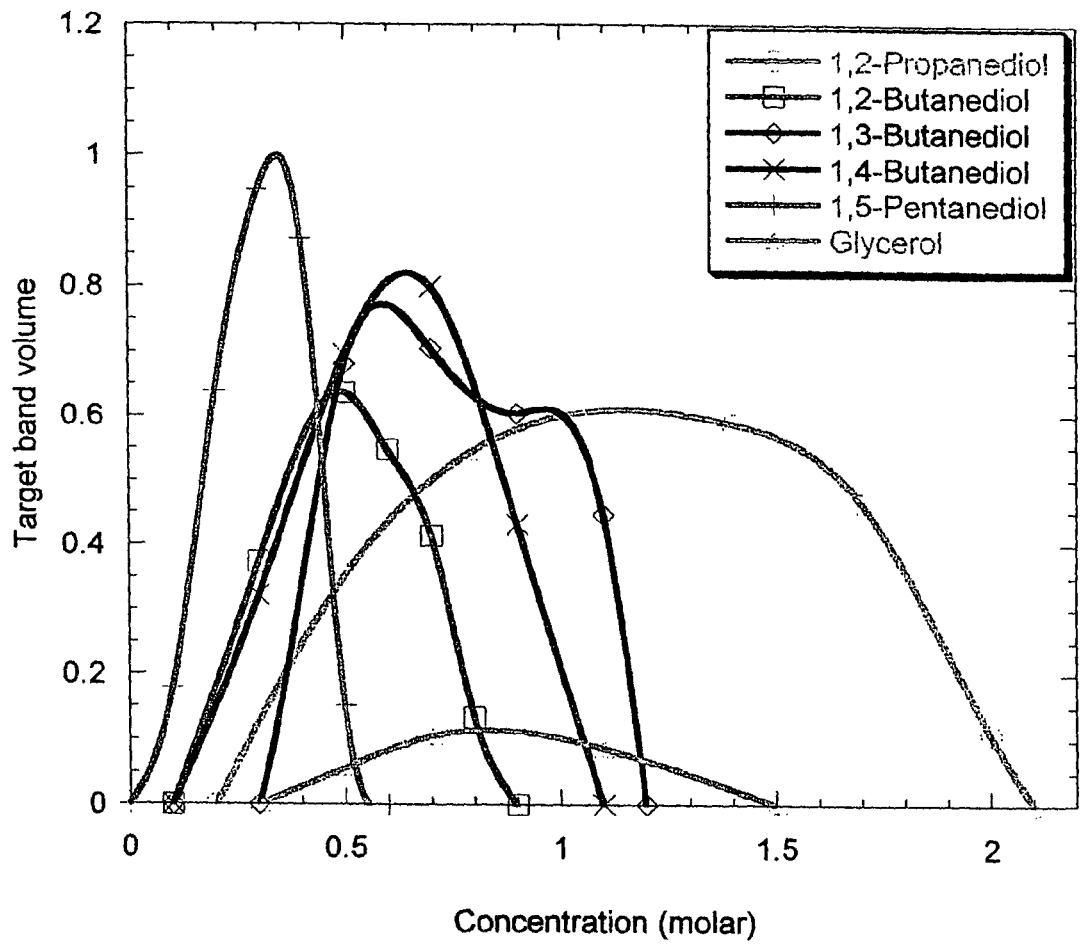
Figure 10 Variation of c-jun amplification with concentration of selected diols and glycerol (standard). Target band volume is normalized to the potency of 1,4-butanediol. Interpolation was carried out by fitting cubic splines to the data.

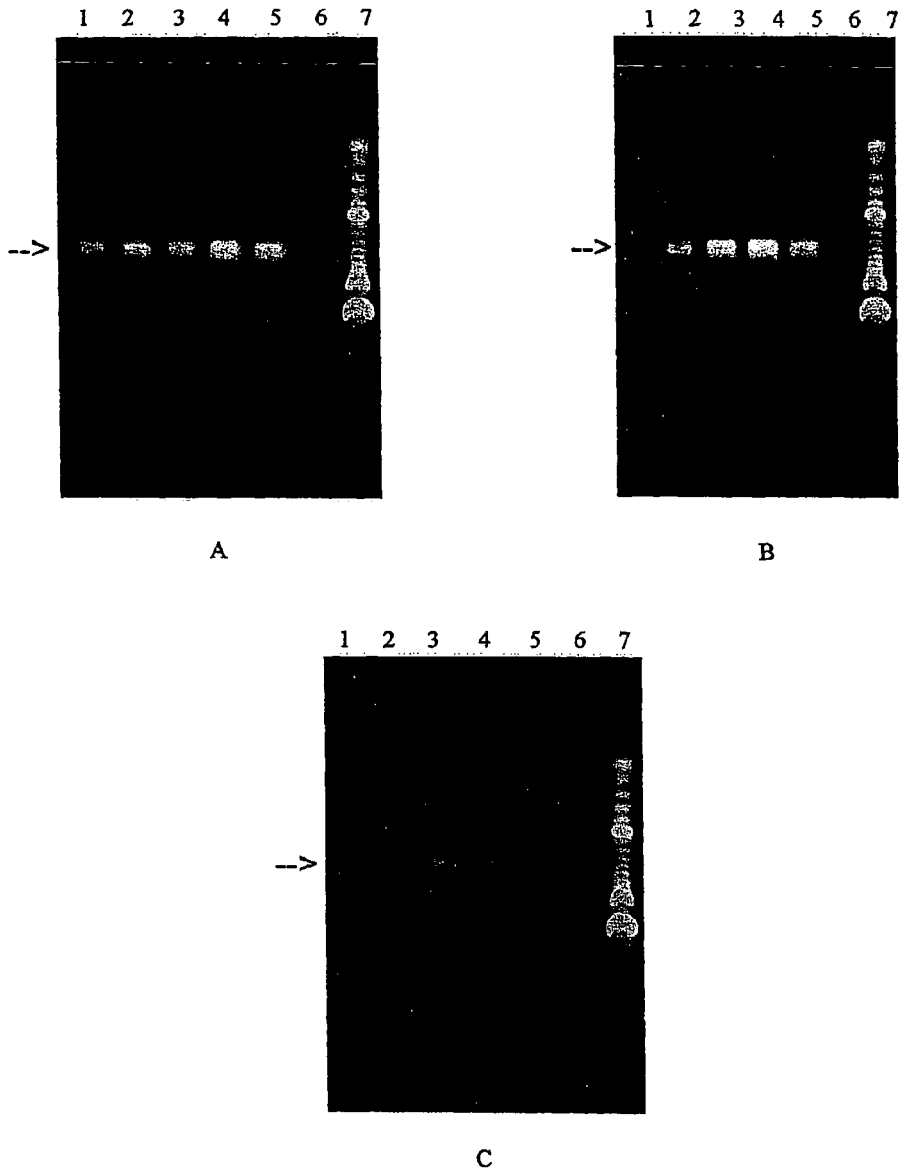

Figure 11 Enhancement of PCR amplification of c-jun (996 bp segment) by 1,2-propanediol, 1,4-butanediol and glycerol (95°C denaturation). A. 1,2-Propanediol (48°C annealing). Lane 1: 0.5M, Lane 2: 0.8M, Lane 3: 1.1M, Lane 4: 1.4M, Lane 5: 1.7M, Lane 6: 2.0M, Lane 7: 100 bp DNA ladder. B. 1,4-Butanediol (50°C annealing). Lane 1: 0.1M, Lane 2: 0.3M, Lane 3: 0.5M, Lane 4: 0.7M, Lane 5: 0.9M, Lane 6: 1.1M; Lane 7: 100 bp DNA ladder. C. Glycerol (58°C annealing). Lane 1: 0.3M, Lane 2: 0.5M, Lane 3: 0.7M, Lane 4: 0.9M, Lane 5: 1.1M, Lane 6: 1.5M; Lane 7: 100 bp DNA ladder. Arrow designates 996 bp.

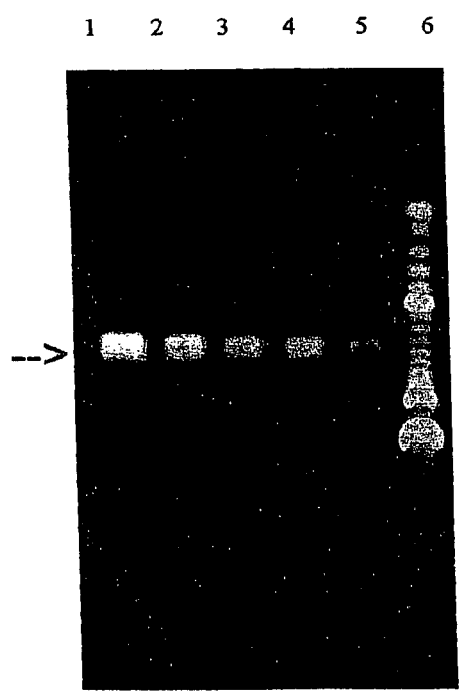
Figure 12. Comparison of best results in the enhancement of PCR amplification of c-jun cDNA (996 bp segment) by diols. Lane 1: 0.3M 1,5-Pentanediol, Lane 2: 0.6M 1,4-Butanediol, Lane 3: 0.5M 1,2-Butanediol, Lane 4: 1.4M 1,2-Propanediol, Lane 5: 0.7M Glycerol, Lane 6: 100 bp DNA ladder. Arrow designates 996 bp.

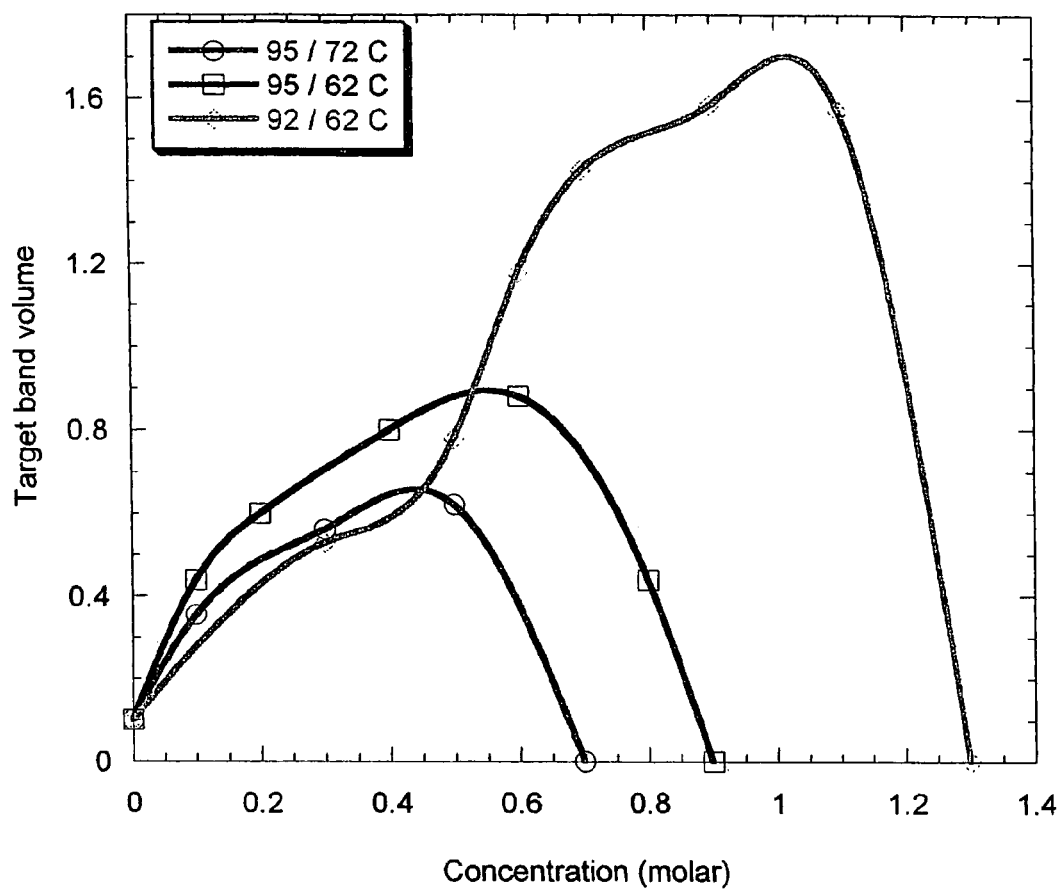

Figure 13 Variation of GTP amplification with concentration of 1,2-butanediol under different cycling conditions: effects of lowering extension and denaturation temperatures. Target band volume is normalized to the potency of 1,5-pentanediol under 95 / 72C conditions. Note increase in potency and cutoff concentration when lower extension and denaturation temperatures are employed.

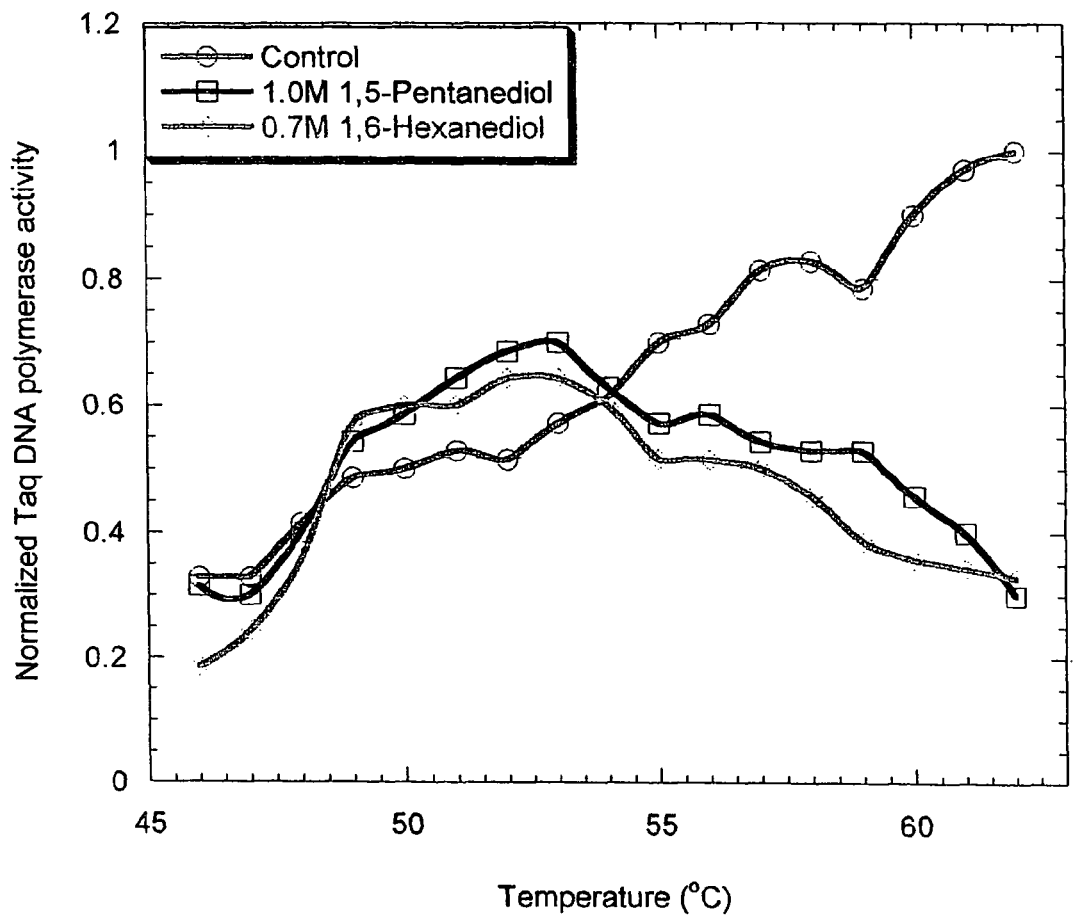
Figure 14 Variation of Taq polymerase activity with temperature in the absence of cosolvents and in the presence of 1.0M 1,5-pentanediol and 0.7M 1,6-hexanediol. Activity is normalized to the control value at 62°C. Note activation of polymerase by solvents in the temperature range 49-53°C. Activation exceeds 25% in the case of 1,5-pentanediol.

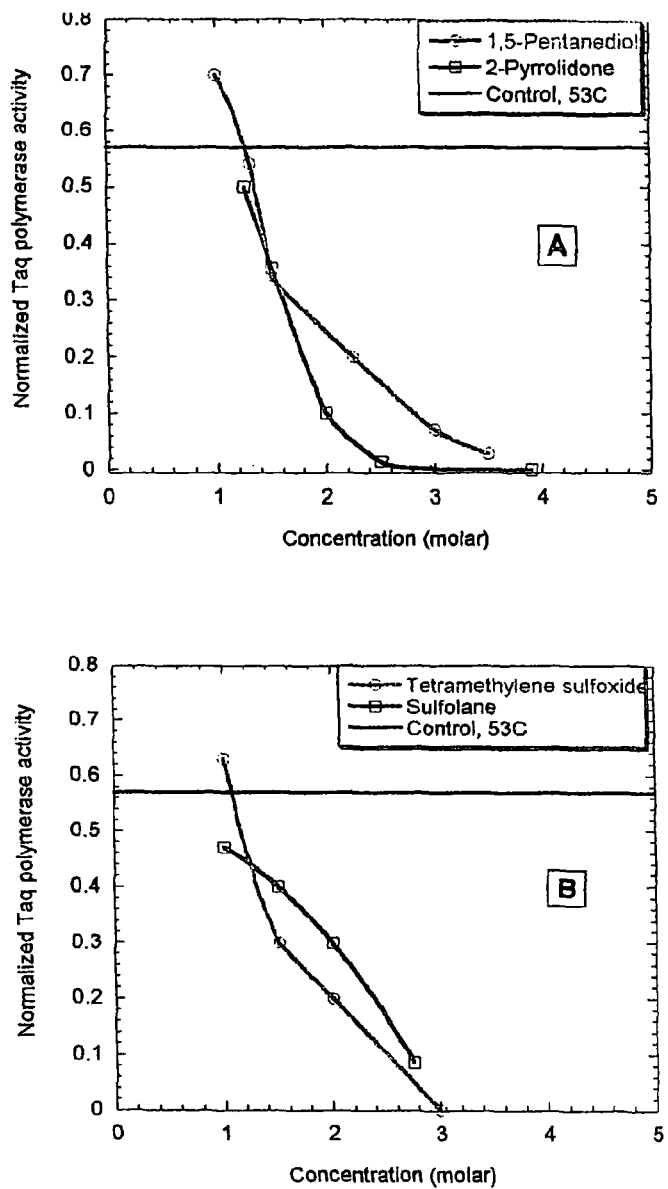

Figure 15 Variation of Taq polymerase activity at 53°C with high concentrations of compounds from the four cosolvent families: A. 1,5-pentanediol and 2-pyrrolidone, B. tetramethylene sulfoxide and sulfolane. Control activity at 53°C is included as a reference. Activity is normalized to the control activity at 62°C. Data points were interpolated rather than fit by linear regression because of the nonlinearity of the activation phenomenon. Note activation by 1,5-pentanediol and tetramethylene sulfoxide at 1M concentration; the interpolation curves suggest the possibility of greater activation at lower concentrations, untested at this temperature.

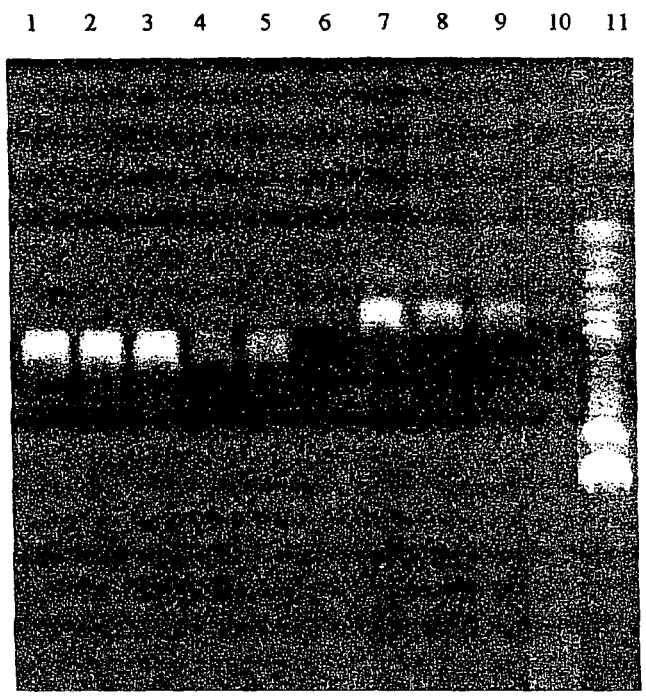

Figure 16 Low temperature PCR amplification and comparison with best results obtained under standard cycling conditions. All low temperature reactions employed a 50°C annealing temperature and 53°C extension temperature. Lanes 1-5: GTP amplification (660 bp). Lane 1: 85°C denaturation, 1.0M 1,5-pentanediol; Lane 2: 85°C denaturation, 1.5M 1,5-pentanediol; Lane 3: 80°C denaturation, 2.0M 1,5-pentanediol; Lane 4: 75°C denaturation, 3.0M 1,5-pentanediol; Lane 5: 95 / 55 / 72 °C, 0.3M 1,5-pentanediol. Lane 6: spacer. Lanes 7-10: PSM amplification (511 bp). Lane 7: 85°C denaturation, 1.5M 1,5-pentanediol; Lane 8: 80°C denaturation, 2.5M 1,5-pentanediol; Lane 9: 95 / 50 / 72 °C, 0.8M 1,3-butanediol; Lane 10: spacer, Lane 11: 100 bp DNA ladder. Note that PCR products were diluted twofold compared to earlier gels in order to facilitate visualization of intensity differences.

SEQUENCE LISTING

<160> NUMBER OF SEQ ID NOS: 8

<210> SEQ ID NO 1
<211> LENGTH: 19
<212> TYPE: DNA

```
<213> ORGANISM: Artificial Sequence
<220> FEATURE:
<223> OTHER INFORMATION: Novel Sequence

<400> SEQUENCE: 1
atgagctccg gccagcagc                                                    19

<210> SEQ ID NO 2
<211> LENGTH: 27
<212> TYPE: DNA
<213> ORGANISM: Artificial Sequence
<220> FEATURE:
<223> OTHER INFORMATION: Novel Sequence

<400> SEQUENCE: 2
tcagtcttcc cattcatcat catcctc                                            27

<210> SEQ ID NO 3
<211> LENGTH: 21
<212> TYPE: DNA
<213> ORGANISM: Artificial Sequence
<220> FEATURE:
<223> OTHER INFORMATION: Novel Sequence

<400> SEQUENCE: 3
atgactgcaa agatggaaac g                                                  21

<210> SEQ ID NO 4
<211> LENGTH: 23
<212> TYPE: DNA
<213> ORGANISM: Artificial Sequence
<220> FEATURE:
<223> OTHER INFORMATION: Novel Sequence

<400> SEQUENCE: 4
tcaaaatgtt tgcaactgct gcg                                                23

<210> SEQ ID NO 5
<211> LENGTH: 18
<212> TYPE: DNA
<213> ORGANISM: Artificial Sequence
<220> FEATURE:
<223> OTHER INFORMATION: Novel Sequence

<400> SEQUENCE: 5
aaacactgct gtggtgga                                                      18

<210> SEQ ID NO 6
<211> LENGTH: 20
<212> TYPE: DNA
<213> ORGANISM: Artificial Sequence
<220> FEATURE:
<223> OTHER INFORMATION: Novel Sequence

<400> SEQUENCE: 6
tagctcaaca gaatccaggc                                                    20

<210> SEQ ID NO 7
<211> LENGTH: 22
<212> TYPE: DNA
<213> ORGANISM: Artificial Sequence
<220> FEATURE:
<223> OTHER INFORMATION: Novel Sequence

<400> SEQUENCE: 7
gaattcgaaa tggcgctgct gg                                                 22
```

```
<210> SEQ ID NO 8
<211> LENGTH: 25
<212> TYPE: DNA
<213> ORGANISM: Artificial Sequence
<220> FEATURE:
<223> OTHER INFORMATION: Novel Sequence

<400> SEQUENCE: 8
ctcgaggtcc agagtacccg ctgtg                                            25
```

CHEMICAL PCR: COMPOSITIONS FOR ENHANCING POLYNUCLEOTIDE AMPLIFICATION REACTIONS

This application is a continuation-in-part of U.S. application Ser. No. 10/056,917 filed Jan. 25, 2002, now U.S. Pat. No. 6,949,368, the entirety of which is herein incorporated by reference, and claims benefit under 35 U.S.C. §119(e)(1) to U.S. provisional applications 60/451,642, filed Mar. 4, 2003, and 60/451,650, also filed Mar. 4, 2003. the entireties of both of which are also herein incorporated by, reference.

Pursuant to 35 U.S.C. §202(c), it is acknowledged that the U.S. government has certain rights in the invention described herein, which was made in part with funds from the National Science Foundation and the National Institutes of Health, Grant No. GM 44038.

FIELD OF THE INVENTION

The present invention relates generally to methods in molecular biology. More particularly, it relates to compositions and methods for enhancing polynucleotide amplification reactions.

BACKGROUND

Polynucleotide amplification reactions have become central techniques of molecular biology. Indeed, many current methods in molecular biology utilize as their first step an amplification reaction involving either DNA or RNA as a template.

The polymerase chain reaction (PCR) and related techniques, such as NASBA (nucleic acid sequence-based amplification), TAS (transcription-based amplification system), 3SR (self-sustained sequence replication), LAR (ligation amplification reaction, Q-beta replicase and LCR (ligase chain reaction) are all methods of polynucleotide amplification. Many of these amplification reactions utilize a polymerase enzyme or fragment of such an enzyme.

Despite their widespread use, however, these techniques are often fraught with difficulties. In many cases, the standard procedure fails to produce meaningful amplification or an amplification at all. In other instances, the amplification of the target sequence is nonspecific, meaning that its amplification is accompanied by similar amplification of non-target polynucleotide fragments (Roux, 1995, in: Dieffenbach & Dveksler, eds., PCR Primer-A Laboratory Manual. Cold Spring Harbor Laboratory Press, Cold Spring Harbor, N.Y., pp. 55-66; Newton & Graham, 1994, PCR. Bios Scientific, Oxford). These problems, especially low yield, can be particularly severe for templates with high GC contents (Varadaraj & Skinner, 1994, Gene 140, 1-5; McDowell et al., 1998, Nucl. Acids Res. 26, 3340-3347).

Accordingly, improvement of amplification and stringency has been the focus of many research efforts. It has been found that various organic additives can often yield significant improvements in this regard, the most successful of the additives tested being DMSO, glycerol, polyethylene glycol, betaine and formamide (Winship, 1989, Nucl. Acids. Res. 17, 1266; Smith et al., 1990 Amplifications 5, 16-17; Weissensteiner & Lanchbury, 1996, BioTechniques 21, 1102-1108).

U.S. Pat. Nos. 5,545,539 and 5,846,716 to Miller et al. disclose a method for improving sequence or amplification of polynucleotides that comprises including a glycine-based osmolyte, such as trimethylglycine, in the amplification or sequencing reaction mixture. Addition of this reagent was reported to be particularly advantageous in reducing the appearance of stutter bands in the amplification product.

U.S. Pat. No. 6,114,150 to Weissman et al. discloses methods and compositions for obtaining uniform amplification of nucleic acid templates with variable G+C content by adding to the reaction mixture a zwitterions and a compound that disrupts base pairing. Compounds such as betaine, monomethyl glycine, dimethylglycine and D-carnitine are disclosed as useful zwitterions; DMSO and formamide are disclosed are useful for disrupting base-pairing.

U.S. Pat. No. 6,300,075 to Preston et al. discloses a method to amplify nucleic acids that is alleged to improve the specificity of amplification of a target nucleic acid. The method comprises supplementing an amplification reaction mixture with a carrier nucleic acid and one or more magnesium salts. Addition of these materials is reported to reduce polymerase extension of non-target nucleic acids during amplification assays through a reduction in the amount of primer-dimer formation prior to raising the temperature of the amplification mixture during thermal cycling.

U.S. Pat. No. 6,261,773 to Segawa et al. discloses that the sensitivity of amplification reactions, particularly of RNA templates, may be improved by adding EDTA or a similar reagent, such as nitriotriacetic acid (NTA), uramil diacetic acid (UDA), trans-1,2-cyclohexanediaminetetraacetic acid (CyDTA), diethylenetriamine-pentaacetic acid (DTPA), ethyleneglycolbis (2-aminoethyl)ether diaminetetraacetic acid (GEDTA) or triethylenetetraminehexaacetic acid (TTHA), or salts thereof, to the reaction mixture. These compounds are reported to improve the signal-to-noise ratio of amplification reactions by significantly inhibiting the occurrence of non-specific amplification reactions.

Despite their general applicability, the performance of the currently available compounds, especially in the case of GC-rich targets, is quite unpredictable. Any given compound often fails to provide adequate improvement over the control (Baskaran et. al., 1996, Genome Methods 6, 633-638).

Thus, increasing the selection of additives that are capable of improving polynucleotide amplification, especially for recalcitrant targets, would be a significant advance in the art of nucleic acid amplification. Such new additives would be of particular benefit by improving both the potency and specificity of the amplification reaction.

SUMMARY OF THE INVENTION

A composition and method for performing a polynucleotide amplification reaction at low temperature, including a polynucleotide amplification reaction mixture into which is incorporated a sufficiently high concentration of a low molecular weight compound selected from the group consisting of amides, sulfones, sulfoxides and diols, to accomplish the amplification at the low temperature.

In another embodiment, a composition and method for enhancing a polynucleotide amplification reaction, including a polynucleotide amplification reaction mixture into which is incorporated a low molecular weight diol in an amount effective to enhance the polynucleotide amplification.

BRIEF DESCRIPTION OF THE DRAWINGS

FIG. 1 illustrates the structures of certain low molecular weight diols utilized in accordance with the present invention in Example 1.

FIG. 2 is a graph illustrating aspects of PCR amplification in accordance with an embodiment of the present invention.

FIG. 3 is a plot illustrating aspects of PCR amplification in accordance with an embodiment of the present invention.

FIG. 4 is a series of concentration gradients illustrating aspects of PCR amplification in accordance with an embodiment of the present invention.

FIG. 5 is a graph illustrating aspects of PCR amplification in accordance with an embodiment of the present invention.

FIG. 6 is a graph illustrating aspects of PCR amplification in accordance with an embodiment of the present invention.

FIG. 7 is a graph illustrating aspects of PCR amplification in accordance with an embodiment of the present invention.

FIG. 8 is a graph illustrating aspects of PCR amplification in accordance with an embodiment of the present invention.

FIG. 9 is a series of concentration gradients illustrating aspects of PCR amplification in accordance with an embodiment of the present invention.

FIG. 10 is a graph illustrating aspects of PCR amplification in accordance with an embodiment of the present invention.

FIG. 11 is a series of concentration gradients illustrating aspects of PCR amplification in accordance with an embodiment of the present invention.

FIG. 12 is a concentration gradient illustrating aspects of PCR amplification in accordance with an embodiment of the present invention.

FIG. 13 is a graph illustrating aspects of PCR amplification in accordance with an embodiment of the present invention.

FIG. 14 is a graph illustrating aspects of PCR amplification in accordance with an embodiment of the present invention.

FIG. 15 is a series of graphs illustrating aspects of PCR amplification in accordance with an embodiment of the present invention.

FIG. 16 is a concentration gradient illustrating aspects of PCR amplification in accordance with an embodiment of the present invention.

DETAILED DESCRIPTION OF THE PREFERRED EMBODIMENTS

The following definitions are provided to aid in construing the claims of the present application:

As used herein, the term "polynucleotide replication" (PR) refers to any reaction in which a second strand of nucleic acid molecule is synthesized using a first strand as a template. These PR reactions generally encompass amplification of the template polynucleotide, as with PCR and related methods, or cDNA synthesis from an RNA template using reverse transcriptase (RT). Thus the terms "polynucleotide amplification" (PA) or "nucleic acid amplification" are also used herein to describe such PR reactions.

A typical PR reaction mix contains a polymerase or fragment thereof or combination of polymerases having specified activity, dNTP's, a template polynucleotide (DNA or RNA), oligonucleotide primers (in most reactions), an appropriate reaction buffer (e.g., Tris-HCl, with $MgCl_2$, for Taq DNA polymerase) and various additives to enhance the amplification of the template polynucleotide. Additives currently in use include formamide, DMSO, betaine, polyethylene glycol, glycerol, tetramethylammonium chloride and certain nonionic surfactants such as TWEEN 20®.

In accordance with the present invention, a variety of new PR reaction additives have been identified. These compounds have been founds superior to currently-used additives for enhancing polynucleotide amplification.

Three criteria are used to determine if a particular additive is advantageous: high-potency, high-specificity and a wide effective range. When results are viewed as bands of electrophoresed amplification products, potency is defined as the maximum densitometric volume of the target band observed at any concentration of an additive. Specificity is defined as the ratio of target band volume to the total volume of all bands, including nonspecific bands, usually expressed as a percentage. The effective range of an additive is defined as the range of concentrations over which the volume of target band amplification is greater than or equal to 50% of its maximum value.

The present invention provides a variety of compositions and methods for enhancing polynucleotide amplification reactions. This application will first discuss those compositions and methods relating particularly to polynucleotide amplification reactions utilizing low molecular weight diols. Then compositions and methods relating to polynucleotide amplification reactions performed at low temperatures (in some cases also utilizing low molecular weight diols) will be discussed. Finally, several examples will be presented.

Monools are known to be strong denaturants of macromolecular structure (Levine, 1963; Thomas and Dill, 1993). While their effectiveness in denaturing DNA is desirable in PCR amplification, their similarly potent ability to denature proteins can result in inhibition of PCR. Polyols, on the other hand, possessing one hydroxyl group for each carbon in the molecule, are known to be weak DNA denaturants (del Vecchio et al., 1999). Though certain polyols have been found to stabilize protein structure (Athes et al., 1999), this effect in itself is not sufficient to enhance PCR. The polyol glycerol has been used to enhance GC-rich template amplification in the past. Examples include the amplifications of the GC-rich segment of crab satellite DNA and the metallothionein 1a-growth hormone fusion gene that were also reported to be enhanced by DMSO (Varadaraj and Skinner, 1994; Pomp and Medrano, 1991). However, glycerol is used far less frequently than either formamide or DMSO, since it usually provides only minimal improvement over the control. The enhancement of crab satellite DNA amplification by glycerol, for example, was less than 25% of that provided by DMSO. The comparatively anemic PCR enhancement afforded by glycerol most likely stems from its weak DNA denaturing capacity. When functional, glycerol is usually found to exert a positive effect on PCR at concentrations between 5-15%.

Data suggested that diols, intermediate between monools and polyols in their polar-nonpolar balance, could possess macromolecular denaturing properties that are optimal for PCR enhancement. Since the balance between DNA and protein denaturing capacities is a subtle issue, a large variety of diols were screened in Example 1 below in order to gain a good perspective on what types of structural arrangements and hydroxyl-carbon ratios are most effective in PCR. The structures of the diols that were studied in this investigation are displayed in FIG. 1. As can be seen, the chosen compounds span the spectrum of low-molecular weight diols. For every chain length, multiple structural isomers were tested in order to determine the effects of relative hydroxyl location on PCR amplification. The simplest readily available cyclic diols, cis-1,2-cyclopentanediol and trans-1,2-cyclopentanediol, were examined to study simultaneously the effects of hydroxyl conformational restriction and cyclic structure on amplification. 2-Methyl-2,4-pentanediol (MPD), a hexanediol structural isomer, was studied as well, so as to include a branched chain diol in the investigation and to determine whether this known stabilizer of certain protein and DNA conformations (Pittz and Timasheff, 1978) exhibited any unique effects. Glycerol was included as a reference standard.

The results of Example 1 below indicate that low molecular-weight diols are significantly more effective in PCR enhancement than glycerol, the state of the art alcohol enhancer. With templates of low to moderate secondary structure, the effectiveness of diol enhancers appears to improve with increasing chain length up to $C_5$; however, the relative location of the hydroxyl groups plays an important role in determining performance. 1,5-pentanediol is the best-performing additive in the case of these targets. For templates with substantial secondary structure, on the other hand, the relative performance of diol enhancers is considerably modified. The fact that even isomeric diols often display dramatically different effects in PCR underscores the subtlety of PCR enhancement.

In accordance with the present invention, a variety of compositions and methods for carrying out polynucleotide amplification reactions under low temperature cycling conditions have also been identified. The methods comprise lowering the temperature of polynucleotide denaturation and extension reactions in the presence of high concentrations of certain organic solvents, including amides, sulfoxides, sulfones, and diols.

A 72° C. extension temperature is almost always used in PCR reactions; however the rate of decline in polymerase activity with additive concentration is greatly diminished at 62° C., 10° C. lower than the standard PCR extension temperature of 72° C. This phenomenon was investigated in the following experiments, with results indicating the utility of the use of low temperature conditions in many PCR reactions.

The inventors studied thoroughly the rates of DNA synthesis by the polymerase at these two temperatures in the absence of cosolvents. The activity of Taq polymerase at 72° C. has been quoted in the literature to be approximately twice that at 62° C. In contrast to the inventors' findings, however, the polymerase activity assays which quote these values employed either nicked double-stranded DNA, in which a portion of a full-length complementary DNA strand primes synthesis, or high melting primers, which did not substantially dissociate at 72° C. (Lawyer et. Al., 1993). These systems, however, are not characteristic of the conditions usually employed in PCR. Typical PCR primer melting temperatures fall in the range of 50-65° C. The melting temperature of mp13 17 mer primer used by the inventors is approximately 60° C. The net rate of DNA synthesis obtained using two different assay formats is compared. In the first format, the enzyme was added to the reaction mixture containing annealed primer-template after the mixture was heated for 1 minute preincubation at 72° C. In the second, the enzyme was added prior to heating the tube. It was found that the rate of synthesis obtained without preincubation was approximately 4 times as great. Similar experiments were carried out at 62° C. At this temperature, the rates of synthesis were found to be identical using both methods. Activity at 62° C. was about twice as great as that at 72° C. without preincubation, and hence about 8 times as great as that at 72° C. with preincubation. These results indicate that a large fraction of primers dissociate from the template at the higher temperature of 72° C. In particular, on the basis of these results and the previously published reports of ½ maximal activity at 62° C., one must conclude that approximately 4 times as many primers are annealed at 62° C. versus 72° C. when Taq polymerase is present in the system from the outset. In addition, the factor of 4 reveals that the polymerase enzyme stabilizes the primer-template hybrid.

The exact activity ratios obtained in these experiments are dependent upon the fact that the prime-template pair utilized by the inventors melts at 60° C. in absence of Taq polymerase. Primer-templates with other melting temperatures will show different relative activities at 62° C. versus 72° C. In order to predict the relative rates of net DNA synthesis by the enzyme at different temperatures using arbitrary primer-template pairs, it will be necessary to understand the thermodynamics of primer-template stabilization by polymerases, so that for a primer melting at a given temperature in the absence of polymerase, the fraction of primers annealed at any temperature in the presence of polymerase can be estimated theoretically. Without intending to be limited by any explanation as to mechanism of action, these results suggest that the activity of thermostable polymerases using free primers that melt at arbitrary temperatures is best described by the combination of two notions: the "native" activity of the polymerase at a given temperature, measured in activity studies using nicked template DNA or high melting primers, and the fraction of primers annealed at that temperature in the presence of the polymerase.

The inventors finding that the rate of decay of polymerase activity with additive concentration is significantly lower at 62° C. that at 72° C. bears similarity to a published observation that the guanidinium hydrochloride concentration producing half-maximal activity decay in the thermostable enzyme T. maratima GADPH increases with decreasing temperature (Rehaber and Jaenicke, 1992). Without intending to be limited by any explanation as to mechanism of action, the latter discovery can be explained as follows. The fact that thermostable enzymes exhibit optimal activity at high temperatures has be attributed the greater hydrophobic core of these enzymes (Wrba et. al., 1990). At low temperatures, the conformation of the enzymes is highly restricted due to the stability of this core, but when the temperature is raised, the conformation loosens. Chemical denaturants, which destabilize the hydrophobic core, also have the effect of loosening enzyme conformation. At high temperatures in the presence of denaturants, the synergistic effect of these two influences both loosening the conformation results in a rapid decay of activity with increasing denaturant concentration. However, at lower temperatures, the temperature-induced loosening effect is smaller and the synergistic effect is not as pronounced. The result is a smaller rate of activity decline with denaturant concentration. Without intending to be limited by any explanation as to mechanism of action, most likely, the smaller rate of decline in Taq polymerase activity at 62° C. versus 72° C. with increasing additive concentration is also attributable to this phenomenon.

The inventors have observed that the use of a 62° C. extension temperature in PCR reactions with cosolvents can extend their effective range, possibly due to two beneficial effects of 62° C. incubation on Taq polymerase activity—namely the greater control activity due to lesser primer dissociation, and the smaller rate of activity decline with increasing additive concentration. Decreased polymerase activity in the presence of high concentrations of cosolvents is usually the primary cause of cutoff in additive potency, at first due to a diminished rate of net DNA synthesis, and eventually, at higher concentrations, due to the inability of a given polymerase molecule to complete syntheses of a single strand within the allotted extension time. Another benefit observed by the inventors was increased additive potency, due to the fact that an upper limit to the number of template molecules that can be replicated per cycle is determined by the fraction of primers that are annealed at the extension temperature.

The use of the optimal temperature of native polymerase activity in PCR reactions facilitated by cosolvents is not an optimal strategy. In the case of Taq polymerase, difficult PCRs carried out in the presence of common cosolvents such as DMSO or formamide are almost always run using 72° C. extension temperature. Lowering the extension temperature will often provide superior results; lowering the denaturation temperature as well will yield even better results. The only potential drawback to the general use of this method is that the native activity of the polymerase is lower at 62° C. than 72° C. For PCR amplification of long templates, the decreased rate of primer elongation can require the use of longer extension times for completion of strand synthesis during the allotted time.

Lowering the denaturation temperature to 92° C. does not increase the cutoff concentration of 1.5-pentanediol to its maximum predicted value under 62° C. extension conditions. While denaturation temperatures below 92° C. are rarely used in PCR reactions, especially in the amplification of GC-rich templates, lowering the denaturation temperature further allows the cutoff concentration to be extended to this maximum. While at lower denaturation temperatures, product yield is generally diminished at the additive concentrations that are optimal at higher denaturation temperatures, due to a lesser degree of DNA melting, yield is even greater at the higher concentrations that are accessible.

Without intending to be limited by any explanation as to mechanism of action, lowering the extension temperature appears to permit the use of lower denaturation temperatures by allowing one to employ the high additive concentrations required to melt the DNA at these temperatures. Hence, lowering extension temperature below 62° C. would decrease the rate of activity decline with additive concentration to an even greater extent. One would expect that this would allow the use of higher cosolvent concentrations without extinguishing activity, which in turn would permit the use of even lower denaturation temperatures.

The inventors carried out a series of low temperature activity assays as confirmation. Without intending to be limited by any explanation as to mechanism of action, the inventors believe that three primary factors contribute to polymerase activity as far as these studies are concerned: 1) decreasing native activity with decreasing temperature due to greater enzyme rigidity at temperatures below the optimal native activity temperature; 2) decreasing rate of decline of polymerase activity with additive concentration with decreasing temperatures, at least up to a point; and 3) decreased primer dissociation at lower temperatures, especially for low melting primers.

The observed polymerase activity at a give additive concentration and a given temperature were believed to be a superposition of these three effects based on the experimental findings. The third effect was assumed to be negligible based on the observation that at 62° C., preincubation does not alter measured activity, meaning that very little primer dissociation is occurring at this temperature. Therefore, decreasing the temperature further would not likely decrease the extent of primer dissociation in any significant way.

The measured polymerase activity, then, is in fact a function of two variables—temperature and additive concentration. The plot of measured activity versus temperature and additive concentration is a two-dimensional surface. While a truly comprehensive search for maximal polymerase activity would entail screening this entire surface, the number of experiments required to do so would of course be impractical. Therefore, polymerase activity was measured first as a function of temperature in the absence of additives and at one given, high additive concentration. The temperature that yielded the maximum activity of the polymerase at that concentration was then targeted for concentration gradient studies.

A critical factor in this scheme is that the rate of decline of polymerase activity with additive concentration will continue to decrease with decreasing temperature below 62° C. This confers a possible additional benefit—enzyme activation. Many mesophilic enzymes are activated by denaturant-induced loosening of the enzyme structure to a level that facilitates enzyme function (Tan and Lovrien, 1971). Without intending to be limited by any explanation as to mechanism of action, it is possible that in the case of thermophilic enzymes, the greater structural rigidity of the molecules at low temperatures makes them particularly prone to activation by denaturants at those temperatures.

A preferred strategy is to lower both the extension and denaturation temperatures in concert. Lowering the extension temperature allows the use of particularly high concentrations of PCR-enhancing additives without significantly compromising the activity of the polymerase. Reducing the denaturation temperature permits these high concentrations to be used, at least in part because the thermostability of the enzyme does not become a limiting factor. Conveniently, using high additive concentrations permits the DNA template to melt at these lower denaturation temperatures.

Low temperature amplification has been attempted in the past, but only with limited success. In their efforts to use mesophilic polymerases in amplification, Lapidot and Fuller have used high concentrations of proline and glycerol, respectively, in PCR reaction buffers (Iakobashvili and Lapidot, 1999; Fuller, 1995). Both of these chemicals are stabilizers of polymerase conformation, and only mild denaturants of DNA; the stabilization is of course necessary to confer thermostability to the mesophilic polymerases. Low denaturation temperatures had to be employed in these experiments because of the very limited thermostability of the enzymes. Klenow fragment of DNA polymerase I was used in conjunction with proline. Approximately 6M proline, close to the limits of solubility, was needed to lower template melting temperature sufficiently for dissociation to occur at the denaturation temperatures used: these temperatures were minimally sufficient to produce amplification. The denaturation temperature could not be increased further to provide greater template melting, since the polymerase rapidly decayed at higher temperatures. The system was therefore highly constrained—there was virtually no choice for modulation of additive concentration or cycling conditions. Low temperature PCR amplification in the presence of glycerol was only possible with the moderately thermostable Bca polymerase because glycerol could not confer sufficient thermostability to mesophilic polymerases. Again, only a narrow range of solvent concentrations and cycling conditions were successful.

A possible limitation to the osmoprotectant/mesophilic enzyme approach to low temperature PCR is that even if significant concentrations of osmoprotectants are used, the thermostability of the mesophilic enzymes can be negligible above 70° C. Since osmoprotectants are only weak DNA denaturing agents, the melting temperature of templates of even moderate GC content can at best be depressed only slightly below this temperature. Therefore, the yield of these reactions, particularly in the case of GC-rich templates, can be low. A possible motivation for using the osmoprotectant/ mesophilic enzyme approach, therefore, given the likelihood that it is less effective than conventional PCR, is to exploit some of the unique properties of mesophilic polymerases. In recent years, however, the number of well-characterized thermostable polymerases has dramatically increased, and virtually every desirable polymerase property is represented within this group. Moreover, the methods of directed evolution can now be used to engineer thermostable polymerases with specialized properties, even if such enzymes do not exist in nature (Ghadessy et. Al., 2001).

In the denaturant/thermostable polymerase form of low temperature PCR described here, no such limitation exists. Denaturants are significantly more potent DNA-melting agents than are osmoprotectants, and thus the melting temperature of even GC-rich DNA's can be lowered considerably. Moreover, the use of a thermostable polymerase with a denaturant allows much higher denaturation temperatures to be employed, so that even if the melting temperature of the template is not depressed below, say, 75° C., a higher temperature, say 80° C., can be used. Thermostable enzymes are extremely stable at temperatures in this range even in the presence of high denaturant concentrations, as demonstrated in the above low temperature amplifications.

An additional possible benefit to using thermostable (rather than mesophilic) polymerases is that secondary structure of DNA can become less stable at the high extension temperatures where their activity is optimal. Moreover, since denaturants are quite effective in dissociating single-stranded DNA secondary structures, the combination of thermostable polymerases with high concentrations of denaturants can provide a superior solution to the problem of secondary-structure induced polymerase pausing.

Finally, low temperature PCR methods using proline can have the significant disadvantage that this compound can have an isostabilizing effect on DNA sequences, resulting in a lesser degree of selectivity between matched and mismatched primer binding sites. Lapidot found that long primers were absolutely necessary to achieve adequate specificity using this method; since flexibility in primer design is critical to a wide variety of PCR applications, this constraint suggests limitations on the generality of the technique.

Denaturants have generally been perceived as detrimental agents as regards the structure and function of macromolecules. With the invention of PCR, it became clear that their effectiveness in denaturing DNA could be beneficial. However, the belief has remained that their effects on proteins are always undesirable. An important finding in the above low temperature PCR studies is that if the appropriate extension temperatures are used, denaturants can in fact have positive effects on both macromolecular components of the reaction—DNA and enzyme. It appears clear from the above results that many thermostable enzymes may have a window of temperatures at which certain denaturants can increase their activity; in the case of Taq polymerase the above experiments indicate a range of 49-53° C. If the extent of activation is great enough, the aforementioned potential problem with using low temperature PCR to amplify long templates can be circumvented.

The paradigm of low temperature PCR inverts the standard approach to solving the problem of GC-rich template amplification. In order to melt GC-rich templates, high denaturation temperatures are usually employed, up to 98 or 99° C. in some cases. The thermostable enzyme industry has thrived on the demand for polymerases that can withstand these temperatures. However, if the melting temperature of a template is, say, 95° C., it is impossible to achieve 100% template denaturation no matter how high the temperature is raised, unless denaturants are used. Low temperature PCR presents a counterintuitive solution: lower both the denaturation and extension temperatures, and use an additive concentration that results in maximal melting at the denaturation temperature employed. Virtually any thermostable polymerase can be used in low temperature PCR, while only a limited selection is available that can withstand extreme denaturation temperatures.

The advantages of lowering PCR temperatures, rather than increasing them, are manifold. As is well known, high denaturation temperatures significantly increase the rate of hydrolytic DNA-damaging side reactions, including depurination, deamination and strand scission. The use of low denaturation temperatures can increase the fidelity, as well as the specificity and yield, of all PCR reactions. A second benefit is more subtle, and stems from the fact that what we refer to as low denaturation temperatures are not in fact particularly low, but are simply not as high as those conventionally used.

Quantitative PCR is a technique by which the concentration of a template is determined through its competitive amplification against a standard template of known concentration. A particularly vexing problem of quantitative PCR is that the GC contents of the competitively amplified templates must be almost identical (Gibson et al., 1996). A possible reason is that even if a template is not what we typically refer to as "GC-rich", it can be only partially dissociated during the denaturation step. DNA melting typically occurs over a range spanning about 10-15° C. on either side of the $T_m$. It has been noted that templates with melting temperatures above 81° C. will be amplified less efficiently in quantitative PCR under standard cycling conditions (Olerup, 1994). At conventional denaturation temperatures of 92-95° C., these templates can be only partially dissociated.

McDowell and colleagues have studied the competitive amplification of templates that use the same pair of primers but have different patterns of GC content in between these primers (McDowell et al., 1998). In these studies, it was found that the overall intervening GC content is not a reliable indicator of amplification efficiency. Sequences with lower overall GC content but containing GC-rich pockets were found to amplify less efficiently. Nonspecific products were formed in these cases. Sequencing of the products revealed that the primary nonspecific product terminated at the GC rich domain. It appears that in templates of this sort, the low GC content regions can denature, allowing the primers to anneal, but the intervening region does not. The polymerase tends to dissociate at this GC-rich sequence. Alternatively, the template may denature completely, but secondary structures can form upon cooling to the extension temperature. It is possible that these same mechanisms are responsible for the nonspecific amplification and low target band amplification observed with PSM.

Thus even templates of moderate overall GC content are often amplified with lower efficiencies than others under standard conditions. A possible solution to this problem is to use chemical agents that lower template melting temperature. McDowell has investigated the use of DMSO and betaine in this regard. DMSO was not found to provide any substantial improvements, but betaine successfully equalized the amplification efficiencies of the two templates.

The failure of DMSO to produce improvements is not surprising. Standard cycling conditions were used in these experiments. Therefore, the effective range of DMSO was quite small. Since DMSO is not a particularly strong DNA denaturant, the $T_m$ depression elicited was not large enough to completely melt the troublesome template. Betaine, on the other hand, isostabilized the two DNAs. As such, it induced both templates to melt equally, albeit incompletely. Equal efficiency was achieved, but efficiency was low. While this solution was sufficient for the purposes of this quantitative PCR, it is certainly not an optimal solution to the problem of GC-bias. Even in quantitative PCR applications, the isostabilization approach will not work universally. Shorter DNAs will still tend to be amplified preferentially over longer ones, since they will retain lower $T_m$s in the presence of isostabilizers.

This problem is not limited to quantitative PCR. The inventors carried out PCR reactions with c-jun in the absence of cosolvents using a 80° C. denaturation temperature. These reactions were carried out in a real-time format, in which total duplex DNA concentration was followed as a function of cycle number by quantitation using the PicoGreen reagent. Despite the fact that 80° C. is significantly below the melting temperature of c-jun, substantial DNA amplification was observed in these control reactions. Concurrently, reactions in the presence of 1.5M 1,5-pentanediol were carried out under the same conditions. The fluorescence of these two types of reactions plateaued at different levels; the maximal control fluorescence was about ⅗ that of the cosolvent-assisted reactions. Plateau occurred at nearly the same cycle number in both cases. Real-time PCR curves for these reactions are displayed in FIG. 2.

This result suggests that low melting templates present in the cDNA are preferentially amplifying, since the c-jun sequence is unavailable for amplification at 80° C. in the absence of cosolvents. The lower level of maximal fluorescence implies that these nonspecific sequences are shorter than c-jun. Plateau occurs possibly because of primer depletion—the same number of primers is required to amplify a given number of DNA sequences, regardless of sequence length. As can be seen, the multiplicative rate of amplification is greater for the control than for the 1.5M 1,5-pentanediol reaction. This is expected, since a greater fraction of the lower melting background DNA dissociates at each step, compared to the GC-rich c-jun template.

Without intending to be limited by any explanation as to mechanism of action, the inventors believe that this type of nonspecific amplification likely occurs in all PCR reactions, even if primer mishybridization does not appear to be a significant problem. If the complementary sequence is unavailable or less readily available, primers will likely anneal to the next most stable sequence. The resulting nonspecific amplification most probably produces a substantial nonspecific DNA background in all PCR reactions, though these nonspecific products may not be visible on gels due to the fact that they are distributed over the range of molecular weights. It thus appears that the yield and specificity of amplification templates of higher GC content suffers even in standard, nonquantitative PCR reactions. Since yield is paramount in standard PCR reactions, the method of isostabilization will not suffice in these applications.

A method of solving the problems of both yield and specificity of higher GC templates is using a denaturation temperature that is more than 10° C. higher than their $T_m$s. For many templates, this is not possible using standard cycling conditions, since the upper limit to denaturation temperature is 100° C. Even in the presence of denaturants, this window is in many cases unattainable using standard conditions, as found by McDowell, since polymerase activity drops to negligible levels at the denaturant concentrations necessary to lower the $T_m$ sufficiently. However, low temperature PCR presents a solution. The high cosolvent concentrations that can be employed by lowering the extension temperature drop the $T_m$ of the GC-rich DNA enough so that a denaturation temperature just above the $T_{SS}$ of the template can be used. This approach provides an advantage over isostabilization in quantitative PCR as well, since shorter DNAs no longer retain an advantage over longer ones.

Significant lowering of the DNA denaturing temperatures is a prerequisite to optimizing yield and specificity of PCR reactions. The high melting temperatures of long DNAs makes PCR in the absence of cosolvents less efficient than in their presence. The chemically induced lowering of template melting temperatures is, therefore, a natural component of the PCR reaction, properly perceived. From this point of view, the approach to PCR described as "low temperature" is perhaps better described as arbitrary temperature, "chemical" PCR, with standard PCR described as "high temperature". Chemists routinely use a wide range of temperatures and reagent types to achieve optimal yield and purity in their reactions. Chemical PCR refers to the treatment of PCR in a manner analogous to chemical reactions. In arbitrary temperature, chemical PCR, two sets of variables can afford the user extensive control over the reaction in terms of yield and side products—a wide range of possible cycling temperature conditions (referred to henceforth as "cycling space") and solvent structure/concentration (referred to as "solvent space").

In a chemical approach to PCR, a significantly greater degree of control over product selectivity is possible. Currently, the only means of achieving selective amplification of the desired product is through primer design. However, primer design cannot in itself provide the optimal degree of selectivity. When properly understood, the cycling parameter and solvent degrees of freedom in chemical PCR should greatly facilitate the isolated amplification of particular targeted products.

PCR specificity bears a strong resemblance to various forms of selectivity that are possible in chemical reactions. In organic chemistry, remarkable degrees of control over enantioselectivity, regioselectivity and chemoselectivity can now be attained. Organic solvents can often provide improved selectivity in certain chemical reactions. However, solvent-based control of selectivity in chemical reactions does not appear to be particularly sensitive to the precise structural features of the solvent, and chemical control is still the method of choice. In PCR, on the other hand, the complexity of macromolecular denaturation by organic compounds implies that the structure-activity relationships in solvent effects are far more subtle, and may thus provide a far greater degree of control. The wide range of PCR enhancing compounds utilized in the above experiments in Examples 2 through 4 represents a library of reagents, analogous to that available to the organic chemist, which may eventually allow for control in PCR specificity that equals, or even exceeds, that achievable in organic reactions.

In addition to the PCR enhancers studied in the above experiments, other additives such as betaine, proline, glycerol and tetramethylammonium chloride (Chevet et al., 1995) should of course be included in the chemical PCR reagent library. However, as we have seen, the optimal strategy for arbitrary temperature PCR is to use thermostable polymerases in conjunction with denaturants, and other compounds such as osmoprotectants and isostabilizers should be employed as additional reagents within this framework. The addition of stabilizers can allow the use of higher denaturation temperatures than could otherwise be possible at high denaturant concentrations. Polymerases that are more thermostable than Taq can also provide improvements in this regard, potentially permitting 90° C. or higher denaturation temperatures to be employed at these concentrations.

Cycling temperature space is intimately connected to solvent space in chemical PCR. In combination, these two parameters can permit exquisite control. However, their relationship is far from simple. In the extension step of PCR, for example, higher temperatures tend to favor the destabilization of single-stranded secondary structures in template DNA, but also tend to decrease the tolerance of the polymerase to denaturants. The determination of the best extension temperature for a particular template/polymerase combination is a complex optimization problem. In order to solve this problem, temperature-solvent concentration surfaces of the sort shown in FIG. 3 have to be searched more comprehensively. One approach is empirically to sample disparate regions of the surface, and then to use interpolation methods, such as two-dimensional cubic spline data processing, to approximate intervening regions in a manner similar to that employed in the additive screening phase. However, the accuracy of this interpolation cannot be guaranteed at this time, and most likely, a greater mechanistic understanding of the effects of PCR enhancers on the monotonic unfolding of thermostable polymerases will be required.

The contributions of polymerase thermoinactivation, duplex DNA melting and secondary structure dissociation to the PCR optimization problem are less complex. Since these are two-state processes, they can be described with thermodynamic parameters that allow their behavior to be predicted with less experimentation. Nonetheless, the effects of each cosolvent in the chemical PCR library on the thermodynamic parameters of DNA melting and secondary structure must be investigated. The sequence-dependence of these modulations is particularly important; their understanding can permit selectivity to be achieved on the basis of solvent choice. The continuation of mechanistic structure-activity studies is, therefore, paramount to the development of chemical PCR. In fact, structure-activity studies on the impact of solvents on nucleic acid secondary structure is expected to have implications for any type of template-based replication reaction, including reverse transcriptase reactions.

Despite the greater simplicity of these latter factors, the overall chemical PCR optimization problem is formidable. Only one solvent concentration can be used in a given reaction; while a particular solvent identity and concentration can be best for the extension step of a particular reaction, it can nonetheless be an undesirable solution to the total problem because of its effects in the denaturation step. However, once the relevant mechanistic parameters are understood, the optimization problem can be solved numerically by extensions of currently existing theoretical models.

The optimization problem is, in a sense, the inverse of the problem of predicting PCR efficiency. Once a correction is made to each of the rate equations to incorporate the sequence-specific effects of additives, the sequence being amplified can be inserted into the model. Since a given additive has a particular set of effects on each of the reaction parameters, the problem can be highly constrained by the available additives. Numerical simulation of the amplification in the presence of each of the possible additives under different concentration and cycling conditions can allow prediction of the optimal chemical and temperature parameters for the reaction.

An important addition to currently existing theoretical models of DNA amplification is competition for primers by background DNA of lower melting temperature than the target sequence. If the melting temperature of the target DNA cannot be lowered sufficiently by chemical means to permit 100% denaturation, it can be necessary quantitatively to account for this competition. Most likely, this will entail an integration of primer annealing stabilities over all possible primer-sequence alignments, with a correction factor added to the stability of each alignment based on how much of that sequence has been made available through the denaturation step.

The sort of quantitative prediction and optimization outlined herein differs fundamentally, of course, from what is conventionally referred to as quantitative PCR, which, as mentioned, uses amplification to determine the concentration of an unknown relative to that of a standard template. In fact, numerical prediction of chemical PCR amplification under optimized conditions can eventually be used to quantitate template concentrations in the absence of standards.

The effectiveness of a compound, such as a low molecular weight diol, to enhance polynucleotide amplification is assessed under defined conditions. Though the compounds are useful for any type of amplification reaction, they are assessed using PCR reactions under the following conditions. One or more of three standard templates are used: a 996 by segment of human myeloid leukocyte c-jun cDNA, a 511 by segment of human prostate-specific membrane antigen (PSM) cDNA, and bovine brain glycolipid transfer protein (GTP) cDNA (660 bp). Following PCR, reaction products are separated, e.g., via agarose gel electrophoresis, and quantified using three measurable parameters: (1) potency, defined as the maximum densitometric volume of the target product at any concentration of the compound; (2) specificity, defined as the ratio of the target product volume to the total volume of all reaction products (usually expressed as a percent); and (3) effective range, defined as the range of concentrations of the compound in which amplification of the target sequence is at least 50% of its maximum value. These values may be normalized to a "standard" compound currently used as a polynucleotide amplification reaction additive, e.g., formamide or DMSO.

Using these parameters, a compound such as a low molecular weight diol is considered suitable for use as an enhancer of polynucleotide amplification when it has a potency of at least 75%, preferably 125%, and most preferably 200% compared with either DMSO or formamide for at least one of the three DNA fragments. It is further preferable that the compound have a specificity of at least 80%, preferably 90%, and most preferably 95% for either GTP or PSM. Finally, the compound preferably has an effective range that spans a minimum interval of 0.1M, i.e., the difference between the upper and lower concentrations in the effective range is at least 0.1M, for instance 0.4-0.5M or 0.6-0.7M. Broader effective ranges, e.g., 0.15M, 0.2M, 0.25M, 0.3M, or beyond can be useful and preferable. However, if a particular reagent demonstrates superior qualities of potency and specificity, its effective range, even if as narrow as, or narrower than, the minimum range of 0.1M, is of lesser importance.

Low molecular weight diols and PR reactions performed using low temperature polynucleotide amplification can be used to enhance synthesis and amplification of any polynucleotide template, including DNA and RNA. They are particularly useful for amplification of polynucleotides with high GC content or regions of secondary structure. In amplification reactions such as PCR, addition of the compounds increases the efficiency of polynucleotide synthesis per round of amplification, especially for GC rich templates. This is of significance because even a slight decrease in efficiency in a single cycle (e.g., 10%) can lead to a large decrease in total product, e.g., 95%. High secondary structure of templates causes pausing and dissociation of the polymerase from the template, leading to non-specific amplification products. Low molecular weight diols and PR reactions performed using low temperature polynucleotide amplification decrease secondary structure of templates, thereby increasing specificity.

Low molecular weight diols are useful as additives in any PR reaction and any PR reaction can be performed using low temperature polynucleotide amplification. These PR reactions include, without limitation, amplification reactions, such as PCR, NASBA (nucleic acid sequence-based amplification), TAS (transcriptase-based amplification system), 3SR (self-sustained sequence replication), LAR (ligation amplification reaction), Q-beta replicase, and LCR (ligase chain reaction). In fact, any polymerase-based reaction involving a template that requires denaturing, e.g., a double stranded template or a single stranded template with secondary structure, will be facilitated by addition of a low molecular weight diol or by performance using low temperature polynucleotide amplification. For instance, in addition to the above amplification reactions, reverse transcriptase (RT) reactions involving RNA templates with secondary structure can be facilitated. Additional specific uses of low molecular weight diols and PR reactions performed using low temperature polynucleotide amplification for polynucleotide synthesis and amplification are described in greater detail later in this section.

It should be noted that any molecular biology technique that incorporates polynucleotide denaturation as a step can be improved by the addition of a low molecular weight diol to enhance denaturing, in a manner similar to the way formamide is currently used. However, reactions that utilize a polymerase or other enzyme require compounds that are more than simply good denaturants: the compounds also must be benign toward the enzymes. As an illustration, urea is a very good denaturant but inhibits polynucleotide amplification reactions because it damages polymerase enzymes. Low molecular weight diols are generally more potent than formamide and therefore can be used at lower concentrations. These compounds have a discernable effective range as described herein. The upper delineation of this range relates in part to inactivation of polymerases at higher concentrations of the compounds.

Thus, low molecular weight diols are used to best advantage in PR reactions that utilize a polymerase or derivative or fragment thereof, alone or in combination with one another or with other enzymes. In a preferred embodiment, the PR reaction is an amplification reaction. In a particularly preferred embodiment, it is a PCR. One aspect of the present invention features an amplification reaction mixture, preferably a PCR mixture, comprising the following ingredients: a polymerase, a template polynucleotide, dNTPs, oligonucleotide primers (in most applications; one exception is RT reactions where the synthesis of DNA is self-priming), a reaction buffer, and one or more enhancing agents (also referred to herein as "reaction adjuvants") comprising compounds selected from the class consisting of low molecular weight diols, amides, sulfones, and sulfoxides.

In thermocycling amplification reactions, the polymerase can be a thermostable polymerase, including but not limited to Taq, Tth, Tme, Tli, and Pfu polymerases or variants thereof. In reactions that do not involve thermocycling, the polymerases can be DNA polymerase I, Klenow fragment, or a reverse transcriptase. Combinations of polymerases include, for example, combinations in which one polymerase lacks a $3^1$-$5^1$ exonuclease activity and another possesses the activity.

Other ingredients of the reaction mixture are well described in the art, for instance, Ausubel et al., Current Protocols in Molecular Biology, John Wiley & Sons, Inc., 2001, and the Examples herein. The template polynucleotide may be single or double stranded DNA, RNA, or heterologous DNA-RNA double strands. Preferably, the template is a sequence between about 50 and 35,000 bases, and can be from various sources, including but not limited to genomic DNA, cDNA, plasmid DNA, viral DNA, DNA fragments, and RNA, as mentioned above.

In reactions utilizing added oligonucleotide primers, preparation and use of such primers is well known in the art. Primers preferably are between about 10 and 30 bases in length. Multiple primers can be added to a single reaction mixture to prime multiple templates or multiple sites on a single template. Such multiplex amplification results in the simultaneous amplification of several targets.

The reaction buffer and additional reaction reagents utilized in PR reactions are well known in the art.

Enhancing agents comprising compounds selected from the class consisting of low molecular weight diols, amides, sulfones, and sulfoxides are added to the reaction mixture at a concentration deemed to be within the effective range of the particular agent, determined by calculation in a reference amplification reaction as described above and in the Examples (effective range calculated as a concentration yielding amplification of the target sequence of at least 50% of the maximum amount achievable by the agent). In a preferred embodiment, the concentration of a selected agent in a reaction mixture is near the peak of its most effective concentration, i.e., yielding amplification of the target sequence of at least 60%, more preferably 70%, yet more preferably 80%, even more preferably 90%, and most preferably 100% of the maximum value achievable by the agent for a selected template.

Once the reaction mixture is assembled, polynucleotide synthesis or amplification is conducted according to methods established for the particular reaction being performed. It will be appreciated by one of skill in the art that such methods are subject to variation and optimization depending upon the type of synthesis/amplification reaction being performed, as well as the target polynucleotide being synthesized. Reaction products are assessed according to standard methods, and as described hereinabove and in the Examples.

The compositions and methods described herein will find broad utility in any technique that employs polynucleotide replication or amplification. A non-exhaustive list of such applications is presented below:

1. Reverse transcriptase PCR—PR-enhancing agents of the invention are useful in both steps; duplication of the mRNA template and PCR of the resulting cDNA.
2. Site-specific mutagenesis.
3. PCR-based labeling of oligonucleotides.
4. RACE (rapid amplification of cDNA ends).
5. Cloning/expression of DNA.

In particular the following applications will be improved by the present invention.

6. Genomic sequencing: many genes have high GC content or occur in regions of the genome GC content is high.
7. DNA computing, which uses an amplification step as a central component.
8. RT reactions on templates with secondary structure.
9. Denaturing Gradient Gel Electrophoresis (DGGE)
10. Medical diagnostics involving amplification of low copy number sequences.
11. Quantitative PCR.
12. Amplification of tandem repeats in a genome.
13. In situ PCR.
14. Forensics where sample size is limited and copy number is low.

The following examples are provided to describe the invention in greater detail. They are illustrate, but not to limit, the invention.

Example 1

Enhancement of Polynucleotide Amplification by Low Molecular Weight Diols

Investigations into the PCR enhancing capabilities of diol cosolvents were carried out in Example 1 and demonstrated the superior effectiveness of diol cosolvents as compared to glycerol in PCR enhancement.

Materials and Methods

Amplification reactions were carried out under the following general conditions. Those skilled in the art will appreciate, however, that to the extent that the conditions (set forth in this application) required for specific experiments described in this example were inconsistent with the following general conditions, limited exceptions to the following general conditions were made The general conditions were as follows: 10 Mm Tris-HCl (Ph 8.8), 50 Mm KCl, 1.5 Mm MgCl2, 0.01% (w/v) gelatin, 0.2 Um primers, 0.06 ng/ul template, 0.2 Mm each Dntp, 0.04 U/ul Taq polymerase. The templates used were bovine brain N-WASP cDNA (1518 bp), a 996 bp segment of human myeloid leukocyte c-jun cDNA, a 511 bp segment of human prostate-specific membrane antigen (PSM) cDNA, and bovine brain glycolipid transfer protein (GTP) cDNA (660 bp). cDNA synthesis was carried out using the FIRST-STRAND® RT-PCR kit from Stratagene on the respective mRNAs purchased from Clontech. All amplification reactions for gene were carried out using a single master batch of cDNA. Taq polymerase and dNTPs were obtained from Stratagene. Primers were obtained from Genosys. Primer melting temperatures ($T_m$s) were calculated using the Genosys oligo calculator program. The sequences of the primers were as follows.

```
N-WASP primer n1:
d(ATGAGCTCCGGCCAGCAGC),         (SEQ ID NO: 1)

primer n2:
d(TCAGTCTTCCCATTCATCATCATCATCCTC); (SEQ ID NO: 2)

c-jun primer j1:
d(ATGACTGCAAAGATGGAAACG);        (SEQ ID NO: 3)

primer j2:
d(TCAAAATGTTTGCAACTGCTG-CG);     (SEQ ID NO: 4)

PSM primer p1:
d(AAACACTGCTGTGGTGGA);           (SEQ ID NO: 5)

primer p2:
d(TAGCTCAAC-AGAATCCAGGC);        (SEQ ID NO: 6)

GTP primer g1:
d(GAATTCGAAATGGCGCTGCTGCTGG);    (SEQ ID NO: 7)

Primer g2:
d(CTCGAGGTCCAGAGTACCCGCTGTG).    (SEQ ID NO: 8)
```

Calculated

Tms of the primers were as follows: n1-72.4° C., n2-70.7° C., j1-63.9° C., j2-70.8° C., p1-60.3° C., p2-61.9° C., g1-73.3° C., g2-74.4° C.

Additive chemicals were obtained from the following sources. N-methylformamide, N, N-dimethylformamide, acetamide, N-methylacetamide, N,N-dimethylacetamide and propionamide were purchased from Acros. 2-pyrrolidone, N-hydroxyethylpyrrolidone and N-methylpyrrolidone were obtained as free samples from BASF Corporation. Isobutyramide was purchased from Aldrich. Formamide was purchased from Gibco-BRL. The diols utilized in Examples 1 through 4 of this application were purchased from Aldrich as well.

Polymerase chain reactions for the N-WASP gene were conducted on a ROBOCYCLER® Gradient 40 thermal cycler from Stratagene using 100 ul solutions in 600 ul thin-walled tubes. For expediency, amplification of c-jun, PSM and GTP was carried out in a ROBOCYCLER® Gradient 96 thermal cycler from Stratagene using 50 ul solutions in 200 ul thin-walled tubes. Prior to Taq polymerase addition, a hotstart protocol was carried out that consisted of an initial cycle of 95° C. for 5 minutes (11) to ensure complete first-strand separation, followed by a cycle of 54° C. for 5 minutes. Amplifications were run for 30 cycles. Denaturation was done for 1 minute at the minimum temperatures that yielded discernable amplification: 92° C. for N-WASP and 95° C. for c-jun, PSM and GTP. Extension was done at 72° C. for periods depending on target length: 2 minutes for N-WASP, 1.5 minutes for c-jun and GTP, and 1 minute for PSM. Annealings were carried out either at fixed concentrations of additives using temperature gradients of 38-56° C. for N-WASP and 44-58° C. for the other targets, or at varying concentrations of additives using fixed temperatures of 41° C. for N-WASP, 50° C. for c-jun and PSM, and 54° C. for GTP.

Amplification products were analyzed by agarose gel electrophoresis on 0.8% agarose gels in which 20 ul reaction products were loaded with 4 ul loading buffer. Gels were stained with ethidium bromide, visualized on a UV transilluminator (Fisher), and documented by photography. Densitometric quantitation of amplification products was carried out using IMAGE SCANNER® and IMAGE MASTER® software from Amersham Pharmacia. Background correction was done using the software's rolling disc method.

Investigations into the PCR enhancing capabilities of diol cosolvents were carried out using GTP as the primary template. This choice was made in order to provide the cosolvents with the greatest opportunity to demonstrate their effectiveness because GTP has the lowest GC content of the three templates used. Whether any diol is exclusively capable of amplifying c-jun at 92° C. was not investigated, since the diol family does not contain any member analogous to tetramethylene sulfoxide or sulfolane. The standard protocol for annealing temperature and concentration gradient screening was again followed. Additives were tested with GTP over annealing temperature gradients using a 95° C. denaturing temperature; 1,2-pentanediol and 1,2-hexanediol displayed detectable amplification only in very narrow concentration ranges, and trans-1,2-cyclopentanediol was inhibitory at all concentrations. These cosolvents were thus omitted from further studies. The optimal annealing temperatures for the remaining compounds were: ethylene glycol, 1,2-propanediol, 1,3-propanediol and cis-1,2-cyclopentanediol—58° C.; 1,2-butanediol—54° C.; 1,3-butanediol and 1,4-butanediol—60° C.; 2,4-pentanediol, 1,5-pentanediol, 1,6-hexanediol and MPD—56° C. The following concentration gradients were tested at these annealing temperatures: ethylene glycol—0.5, 1.0, 1.5, 2.0, 2.5, 3.0 and 4.5M; 1,2-propanediol—0.3, 0.5, 0.7, 0.9, 1.1, 1.4, 1.6, 1.8 and 2.0M; 1,3-propanediol—0.3, 0.5, 0.7, 0.9, 1.1 and 1.4M; 1,2-butanediol—0.1, 0.3, 0.5, 0.7, 0.8, 0.9 and 1.1M; 1,3-butanediol—0.2, 0.4, 0.5, 0.6, 0.7, 0.8, 1.0 and 1.1M; 1,4-butanediol—0.2, 0.4, 0.5, 0.6, 0.7, 0.8 and 1.0M; 1,5-pentanediol—0.1 to 0.6M in 0.1M intervals; 2,4-pentanediol—0.1 to 0.6 in 0.1M intervals; 1,6-hexanediol—0.05 to 0.35M in 0.05M intervals; MPD—0.1 to 0.5M in 0.1M intervals; cis-1,2-cyclopentanediol—0.05 to 0.3M in 0.05M intervals; glycerol—0.1 to 1.3M in 0.2M intervals. FIG. 4 shows results from the concentration gradients for 1,2-butanediol, 1,2-propanediol and glycerol. Potencies and effective ranges of the cosolvents are listed in Table 1. Virtually every diol studied provided nearly 100% specificity with GTP; thus, specificities are omitted from the table. Variation of amplification with concentration is displayed for 1,2-propanediol, 1,4-butanediol, 1,5-pentanediol and glycerol in FIG. 5. Splines for the three isomeric butanediols are shown in FIG. 6.

Though a large number of diols were found to be effective enhancers of GTP amplification, in order to maintain the number of experiments at a manageable level, only selected groups of compounds were tested with PSM and c-jun. With PSM, 1,2-propanediol, 1,2-butanediol, 1,3-butanediol, 1,4-butanediol and glycerol were tested; with c-jun, ethylene glycol and 1,3-propanediol were also tested in addition to these compounds. Annealing temperature gradient studies identified the following optimal temperatures for the additives in the case of PSM: 1,2-propanediol, 1,2-butanediol, 1,5-pentanediol and glycerol—52° C.; 1,3-butanediol—50° C.; 1,4-butanediol—54° C. The following additive concentrations were tested using these annealing temperatures: 1,2-propanediol—0.5, 0.8, 1.1, 1.4, 1.7 and 2.0M; 1,2-butanediol—0.1, 0.3, 0.5, 0.6, 0.7 and 0.8M; 1,3-butanediol—0.1, 0.3, 0.5, 0.6, 0.9, 1.1, 1.2M; 1,4-butanediol—0.1 to 1.1M in 0.2M intervals; 1,5-pentanediol—0.1-0.6M in 0.1M intervals; glycerol—0.5 to 1.9M in 0.2M intervals, and 2.2M. Yield is plotted versus additive concentration for 1,2-propanediol, 1,3-butanediol, 1,5-pentanediol and glycerol in FIG. 7; the spline fits for the three butanediols are shown in FIG. 8. Selected results from the concentration gradients of 1,3-butanediol, 1,5-pentanediol and glycerol are shown in FIG. 9. Potencies, specificities and effective ranges are listed in Table 2. For c-jun, the optimal annealing temperatures were: ethylene glycol—52° C.; 1,2-propanediol, 1,3-propanediol, 1,2-butanediol, 1,3-butanediol and 1,4-butanediol—50° C.; 1,5-pentanediol—54° C.; glycerol—58° C. The following concentrations were tested: ethylene glycol—0.5 to 4.0M in 0.5M intervals; 1,2-propanediol—0.2, 0.5, 0.8, 1.1, 1.4, 1.7, 2.0 and 2.1M; 1,3-propanediol—0.3, 0.5, 0.7, 0.9, 1.1 and 1.4M; 1,2-butanediol—0.1, 0.3, 0.5, 0.6, 0.7; 0.8 and 0.9M; 1,3-butanediol—0.3, 0.5, 0.7, 0.9, 1.1 and 1.2M; 1,4-butanediol—0.3 to 1.1M in 0.1M intervals; 1,5-pentanediol—0.1 to 0.6M in 0.1M intervals; glycerol—0.3, 0.5, 0.7, 0.9, 1.1 and 1.5M. Cubic spline fits to the data points are displayed for selected additives in FIG. 10; results from the 1,2-propanediol, 1,4-butanediol and glycerol concentration gradients are shown in FIG. 11. FIG. 12 compares the best amplifications attained with selected compounds. In addition to the standard RT-PCR studies, the inventors investigated whether the additives were functional in the enhancement of genomic DNA amplification as well. Genomic DNA preparations generally contain a much higher concentration of background DNA than do cDNA preparations. This can increase the probability of primer mishybridization, which can result in decreased product yield. In light of the importance of genomic DNA amplification in the cycle sequencing of genomes, the inventors sought to verify that the additives characterized are effective in its enhancement. In these studies, a 1026 by segment of the Thy-1 gene from rat genomic DNA was amplified. Yield under 92° C. denaturing conditions was low in the absence of additives. 0.6M 1,3-butanediol and 1.5M ethylene glycol, which were near the most effective concentrations of these additives in the RT-PCR studies, were tested with this template over 39-46° C. annealing temperature gradients. Both compounds were found to improve amplification yield, with 1,3-butanediol providing particularly dramatic improvement (data not shown).

Results

A comparison of the diol amplification data in the case of GTP (Table 1) shows that 1,5-pentanediol performs best in the case of this template, followed closely by cis-1,2-Cyclopentanediol. 1,3-Butanediol and 1,4-butanediol are somewhat less effective, although they display wider effective ranges. Among the butanediols, 1,2-butanediol exhibits both the lowest potency and the narrowest effective range. 1,2-Propanediol is slightly more potent, and is distinguished by its extensive range, second only to that of ethylene glycol. The hexanediols—1,6-hexanediol and MPD—both exhibit very narrow ranges. 1,3-Propanediol is the least effective diol enhancer of GTP amplification. Nevertheless, it is still more effective than the state of the art alcohol PCR enhancer, glycerol, which performed quite poorly here.

In the case of c-jun (Table 3), 1,5-pentanediol performs best. 1,4-Butanediol and 1,3-butanediol are now more clearly distinguished, but again, both are significantly more effective than their isomer 1,2-butanediol. The relative order of 1,2-butanediol and 1,2-propanediol is now reversed in terms of potency. However, the latter is still a more effective additive overall, due to its wide range. 1,3-Propanediol remains the least potent diol enhancer. Once again, the state-of-the art glycerol is far less effective than any of the diols tested. The order of effective ranges for c-jun is essentially identical to that observed with GTP.

The differentiation of additive potencies is greatest with PSM (Table 2); each diol is clearly distinguished from the others with this template. The order of effectiveness of the compounds, however, is noticeably altered. 1,3-Butanediol is now the most potent enhancer. 1,4-Butanediol ranks second among the butanediols; 1,2-butanediol again ranks third. 1,2-Propanediol now performs considerably better than 1,2-butanediol. 1,5-pentanediol, clearly the most effective additive with the other two templates, is substantially less potent with PSM. With regard to specificity, however, 1,5-pentanediol performs especially well, joining 1,3-butanediol at the top of the list. Glycerol is again the least effective enhancer, both in terms of yield and specificity.

In summary, low molecular-weight diols are significantly more effective in PCR enhancement than glycerol, the state of the art alcohol enhancer. With templates of low to moderate secondary structure, the effectiveness of diol enhancers appears to improve with increasing chain length up to $C_5$; however, the relative location of the hydroxyl groups plays an important role in determining performance. 1,5-pentanediol is the best-performing additive in the case of these targets. For templates with substantial secondary structure, on the other hand, the relative performance of diol enhancers is considerably modified. In this respect, our diol results differ from those obtained with amides, sulfoxides and sulfones, where in each case one compound stood out clearly from the rest. The fact that even isomeric diols often display dramatically different effects in PCR underscores the subtlety of PCR enhancement.

TABLE 1

Potency and effective range of diols (GTP)

| Additive | Potency[1] | Effective range[2] (molar) |
|---|---|---|
| Ethylene glycol | 0.62 | 1.55-3.55 |
| 1,2-Propanediol | 0.64 | 0.52-1.79 |
| 1,3-Propanediol | 0.39 | 0.31-1.18 |
| 1,2-Butanediol | 0.57 | 0.08-0.62 |
| 1,3-Butanediol | 0.85 | 0.29-0.96 |
| 1,4-Butanediol | 0.87 | 0.16-0.77 |
| 1,2-Pentanediol | NA | NA |
| 2,4-Pentanediol | 0.61 | 0.25-0.70 |
| 1,5-Pentanediol | 1.00 | 0.16-0.47 |
| cis-1,2-Cyclopentanediol | 0.91 | 0.13-0.35 |

TABLE 1-continued

Potency and effective range of diols (GTP)

| Additive | Potency[1] | Effective range[2] (molar) |
|---|---|---|
| trans-1,2-Cyclopentanediol | NA | NA |
| 1,2-Hexanediol | NA | NA |
| 1,6-Hexanediol | 0.80 | 0.13-0.29 |
| 2-Methyl-2,4-Pentanediol | 0.45 | 0.12-0.33 |
| Glycerol | 0.28 | 0.26-1.17 |
| Control | 0.10 | NA |

[1]Normalized maximum densitometric volume of target band: 1,5-Pentanediol = 1.
[2]Concentration interval over which densitometric volume of target band is at least 50% of maximum volume.

TABLE 2

Potency, specificity and effective range of selected diols (PSM)

| Additive | Potency[1] | Specificity[2] | Effective range[3] (molar) |
|---|---|---|---|
| 1,2-Propanediol | 0.75 | 89% | 0.65-1.40 |
| 1,2-Butanediol | 0.42 | 92% | 0.34-0.73 |
| 1,3-Butanediol | 1.00 | 94% | 0.55-1.03 |
| 1,4-Butanediol | 0.65 | 92% | 0.38-0.80 |
| 1,5-Pentanediol | 0.54 | 94% | 0.31-0.49 |
| Glycerol | 0.22 | 83% | 1.10-1.63 |
| Control | 0.11 | 29% | NA |

[1]Normalized maximum densitometric volume of target band: 1,3-Butanediol = 1.
[2]Best specificity (densitometric volume of target as percent of total volume) over the effective range.
[3]Concentration interval over which densitometric volume of target is at least 50% of maximum.

TABLE 3

Potency and effective range of selected diols (c-jun)

| Additive | Potency[1] | Effective range[2] (molar) |
|---|---|---|
| Ethylene glycol | 0.58 | 0.71-3.10 |
| 1,2-Propanediol | 0.60 | 0.43-1.87 |
| 1,3-Propanediol | 0.25 | 0.59-0.96 |
| 1,2-Butanediol | 0.64 | 0.27-0.74 |
| 1,3-Butanediol | 0.77 | 0.40-1.12 |
| 1,4-Butanediol | 0.82 | 0.35-0.91 |
| 1,5-Pentanediol | 1.00 | 0.17-0.45 |
| Glycerol | 0.13 | 0.50-1.25 |
| Control | 0.00 | NA |

[1]Normalized maximum densitometric volume of target band: 1,5-Pentanediol = 1.
[2]Concentration interval over which densitometric volume of target band is at least 50% of maximum volume.

Example 2

Enhancement of Polynucleotide Amplification by Lowering PCR Extension and Denaturation Temperatures in the Presence of Organic Solvents Investigations into the PCR enhancing capabilities of lowering PCR extension and denaturation temperatures in the presence of organic solvents were carried out in Example 2 and demonstrated the superior effectiveness of the lower extension and denaturation temperatures in PCR enhancement.

Materials and Methods

Amplification reactions were carried out under the following general conditions. Those skilled in the art will appreciate, however, that to the extent that the conditions (set forth in this application) required for specific experiments described in this example were inconsistent with the following general conditions, limited exceptions to the following general conditions were made The general conditions were as follows: 10 Mm Tris-HCl (Ph 8.8), 50 Mm KCl, 1.5 Mm MgCl2, 0.01% (w/v) gelatin, 0.2 Um primers, 0.06 ng/ul template, 0.2 Mm each Dntp, 0.04 U/ul Taq polymerase. The templates used were bovine brain N-WASP cDNA (1518 bp), a 996 by segment of human myeloid leukocyte c-jun cDNA, a 511 by segment of human prostate-specific membrane antigen (PSM) cDNA, and bovine brain glycolipid transfer protein (GTP) cDNA (660 bp). cDNA synthesis was carried out using the FIRST-STRAND® RT-PCR kit from Stratagene on the respective mRNAs purchased from Clontech. All amplification reactions for gene were carried out using a single master batch of cDNA. Taq polymerase and dNTPs were obtained from Stratagene. Primers were obtained from Genosys. Primer melting temperatures ($T_m$s) were calculated using the Genosys oligo calculator program. The sequences of the primers were as follows.

```
N-WASP primer n1:
d(ATGAGCTCCGGCCAGCAGC),           (SEQ ID NO: 1)

primer n2:
d(TCAGTCTTCCCATTCATCATCATCATCCTC); (SEQ ID NO: 2)

c-jun primer j1:
d(ATGACTGCAAAGATGGAAACG);          (SEQ ID NO: 3)

primer j2:
d(TCAAAATGTTTGCAACTGCTG-CG);       (SEQ ID NO: 4)

PSM primer p1:
d(AAACACTGCTGTGGTGGA);             (SEQ ID NO: 5)

primer p2:
d(TAGCTCAAC-AGAATCCAGGC);          (SEQ ID NO: 6)

GTP primer g1:
d(GAATTCGAAATGGCGCTGCTGCTGG);      (SEQ ID NO: 7)

Primer g2:
d(CTCGAGGTCCAGAGTACCCGCTGTG).      (SEQ ID NO: 8)
```

Calculated

Tms of the primers were as follows: n1-72.4° C., n2-70.7° C., j1-63.9° C., j2-70.8° C., p1-60.3° C., p2-61.9° C., g1-73.3° C., g2-74.4° C.

Additive chemicals were obtained from the following sources. N-methylformamide, N,N-dimethylformamide, acetamide, N-methylacetamide, N,N-dimethylacetamide and propionamide were purchased from Acros. 2-pyrrolidone, N-hydroxyethylpyrrolidone and N-methylpyrrolidone were obtained as free samples from BASF Corporation. Isobutyramide was purchased from Aldrich. Formamide was purchased from Gibco-BRL.

Polymerase chain reactions for the N-WASP gene were conducted on a ROBOCYCLER® Gradient 40 thermal cycler from Stratagene using 100 ul solutions in 600 ul thin-walled tubes. For expediency, amplification of c-jun, PSM and GTP was carried out in a ROBOCYCLER® Gradient 96 thermal cycler from Stratagene using 50 ul solutions in 200 ul thin-walled tubes. Prior to Taq polymerase addition, a hotstart protocol was carried out that consisted of an initial cycle of 95° C. for 5 minutes (11) to ensure complete first-strand separation, followed by a cycle of 54° C. for 5 minutes. Amplifications were run for 30 cycles. Denaturation was done for 1 minute at the minimum temperatures that yielded discernable amplification: 92° C. for N-WASP and 95° C. for c-jun, PSM and GTP. Extension was done at 72° C. for periods depending on target length: 2 minutes for N-WASP, 1.5 minutes for c-jun and GTP, and 1 minute for PSM. Annealings were carried out either at fixed concentrations of additives using temperature gradients of 38-56° C. for N-WASP and 44-58° C. for the other targets, or at varying concentrations of additives using fixed temperatures of 41° C. for N-WASP, 50° C. for c-jun and PSM, and 54° C. for GTP.

Amplification products were analyzed by agarose gel electrophoresis on 0.8% agarose gels in which 20 ul reaction products were loaded with 4 ul loading buffer. Gels were stained with ethidium bromide, visualized on a UV transilluminator (Fisher), and documented by photography. Densitometric quantitation of amplification products was carried out using IMAGE SCANNER® and IMAGE MASTER® software from Amersham Pharmacia. Background correction was done using the software's rolling disc method.

Two phases of investigations were carried out into the use of 62° C. extension temperature in PCR reactions. The first involved concentration gradients with 1,2-butanediol and 1,5-pentanediol employing 62° C. extension and 95° C. denaturation. The first template used was GTP. A larger range of concentrations was employed than usual in the experiments due to the anticipated increase in effective range. These concentrations were: 0.1, 0.31, 0.5, 0.6, 0.8, 0.9 and 1.1M for 1,2-butanediol and 0.01, 0.2, 0.3, 0.4, 0.5, 0.7 and 1.0M for 1,5-pentanediol. The second phase of investigation involved experiments in which the denaturation temperature was lowered to 92° C. The following concentrations were tested: 1,2-butanediol—0.1, 0.3, 0.5, 0.6, 0.7, 0.9, 1.1, 1.3, and 1.4M; 1,5-pentanediol: 0.1, 0.2, 0.3, 0.4, 0.5, 0.7, 1.0, and 1.4M. 1,2-butanediol was also tested with the more GC-rich template c-jun. The following concentrations were tested: 0.1, 0.3, 0.5, 0.7, 0.9, 1.1, 1.4M.

Results

Table 4 displays the results of the first phase of experiments in terms of potency and effective range. As can be seen, lowering the extension temperature resulted in both increased potency and range for both additives. The cutoff concentration, however, does not correlate in either case with the concentration of activity extinction. It is possible that this discrepancy was due to the greatly diminished thermostability of the polymerase at the cutoff concentrations. Based on thermodynamic data, Taq polymerase in the absence of template is predicted to have a half-life of about 8 seconds at 95° C. in the presence of 0.9M 1,2-butanediol and 10 seconds in the presence of 0.6M 1,5-pentanediol. These values will be increased in the presence of template, but will still be very low, especially during the initial cycles when template concentration is limited.

Potency and effective range data from the second phase of experiments are also listed in Table 4. The results demonstrate that thermostability was indeed the source of cutoff in effective range under 95° C. denaturing conditions. In the case of 1,5-pentanediol, thermostablity remains the determining factor at 92° C., since activity is not entirely diminished at the cutoff concentration (1.0M) of this additive. The inventors have found an approximately linear variation of thermodeactivation AG with 1,5-pentanediol concentrations up to 0.6M; it appears that at 1.0M concentration, decreases, perhaps significantly. Variation of amplification yield with concentration of 1,2-butanediol is displayed graphically for 95/72° C., 95/62° C. cycling conditions in FIG. 13.

Finally Table 4 illustrates the results of testing 1,2-butanediol with the more GC-rich template c-jun, which we found impossible to amplify in the presence of diols using a 92° C. denaturation temperature and 72° C. extension temperature. High product yield was obtained when the extension temperature was lowered to 62° C.

These results reveal that the use of the optimal temperature of native polymerase activity in PCR reactions facilitated by cosolvents is not an optimal strategy. In the case of Taq polymerase, difficult PCRs carried out in the presence of common cosolvents such as DMSO or formamide are almost always run using 72° C. extension temperature. The above results indicate that lowering the extension temperature will often provide superior results; lowering the denaturation temperature as well will yield even better results. The only potential drawback to the general use of this method is that the native activity of the polymerase is lower at 62° C. than 72° C. For PCR amplification of long templates, the decreased rate of primer elongation can require the use of longer extension times for completion of strand synthesis during the allotted time.

TABLE 4

Potency and effective range of selected diols using lower denaturation/extension temperatures

| Template | Additive | Cycling conditions[a] | Potency[b] | Effective |
|---|---|---|---|---|
| GTP | 1,2-Butanediol | 95/62° C. | 0.88 | 0.10-0.82 |
|  |  | 92/62° C. | 1.50 | 0.50-1.27 |
|  | 1,5-Pentanediol | 95/62° C. | 1.49 | 0.15-0.63 |
|  |  | 92/62° C. | 1.97 | 0.29-0.90 |
| c-jun | 1,2-Butanediol | 92/72° C. | 0.00 | NA |
|  |  | 92/62° C. | 0.91 | 0.72-1.02 |

[a]Denaturation/extension temperatures shown; annealing temperatures were 55° C. for GTP, 50° C. for c-jun.
[b]Normalized maximum densitometric volume of target band - 1,5-pentanediol (95/72° C.) = 1.
[c]Concentration interval over which densitometric volume of target band minus control is at least 50% of maximum volume.

Example 3

Enhancement of Polynucleotide Amplification with Low Temperature Polymerase Activity Studies Investigations into the PCR enhancing capabilities of further lowering PCR extension and denaturation temperatures to temperatures lower than those utilized in Example 2 were carried out in Example 3 and demonstrated the superior effectiveness of the lower extension and denaturation temperatures in PCR enhancement.

Materials and Methods

Amplification reactions were carried out under the following general conditions. Those skilled in the art will appreciate, however, that to the extent that the conditions (set forth in this application) required for specific experiments described in this example were inconsistent with the following general conditions, limited exceptions to the following general conditions were made The general conditions were as follows: 10 Mm Tris-HCl (Ph 8.8), 50 Mm KCl, 1.5 Mm MgCl2, 0.01% (w/v) gelatin, 0.2 Um primers, 0.06 ng/ul template, 0.2 Mm each Dntp, 0.04 U/ul Taq polymerase. The templates used were bovine brain N-WASP cDNA (1518 bp), a 996 by segment of human myeloid leukocyte c-jun cDNA, a 511 by segment of human prostate-specific membrane antigen (PSM) cDNA, and bovine brain glycolipid transfer protein (GTP) cDNA (660 bp). cDNA synthesis was carried out using the FIRST-STRAND® RT-PCR kit from Stratagene on the respective mRNAs purchased from Clontech. All amplification reactions for gene were carried out using a single master batch of cDNA. Taq polymerase and dNTPs were obtained from Stratagene. Primers were obtained from Genosys. Primer melting temperatures ($T_m$s) were calculated using the Genosys oligo calculator program. The sequences of the primers were as follows.

```
N-WASP primer n1:
d(ATGAGCTCCGGCCAGCAGC),          (SEQ ID NO: 1)

primer n2:
d(TCAGTCTTCCCATTCATCATCATCATCCTC); (SEQ ID NO: 2)

c-jun primer j1:
d(ATGACTGCAAAGATGGAAACG);        (SEQ ID NO: 3)

primer j2:
d(TCAAAATGTTTGCAACTGCTG-CG);     (SEQ ID NO: 4)

PSM primer p1:
d(AAACACTGCTGTGGTGGA);           (SEQ ID NO: 5)

primer p2:
d(TAGCTCAAC-AGAATCCAGGC);        (SEQ ID NO: 6)

GTP primer g1:
d(GAATTCGAAATGGCGCTGCTGCTGG);    (SEQ ID NO: 7)

Primer g2:
d(CTCGAGGTCCAGAGTACCCGCTGTG).    (SEQ ID NO: 8)
```

Calculated

Tms of the primers were as follows: n1-72.4° C., n2-70.7° C., j1-63.9° C., j2-70.8° C., p1-60.3° C., p2-61.9° C., g1-73.3° C., g2-74.4° C.

Additive chemicals were obtained from the following sources. N-methylformamide, N, N-dimethylformamide, acetamide, N-methylacetamide, N,N-dimethylacetamide and propionamide were purchased from Acros. 2-pyrrolidone, N-hydroxyethylpyrrolidone and N-methylpyrrolidone were obtained as free samples from BASF Corporation. Isobutyramide was purchased from Aldrich. Formamide was purchased from Gibco-BRL.

Polymerase chain reactions for the N-WASP gene were conducted on a ROBOCYCLER® Gradient 40 thermal cycler from Stratagene using 100 ul solutions in 600 ul thin-walled tubes. For expediency, amplification of c-jun, PSM and GTP was carried out in a ROBOCYCLER® Gradient 96 thermal cycler from Stratagene using 50 ul solutions in 200 ul thin-walled tubes. Prior to Taq polymerase addition, a hotstart protocol was carried out that consisted of an initial cycle of 95° C. for 5 minutes (11) to ensure complete first-strand separation, followed by a cycle of 54° C. for 5 minutes. Amplifications were run for 30 cycles. Denaturation was done for 1 minute at the minimum temperatures that yielded discernable amplification: 92° C. for N-WASP and 95° C. for c-jun, PSM and GTP. Extension was done at 72° C. for periods depending on target length: 2 minutes for N-WASP, 1.5 minutes for c-jun and GTP, and 1 minute for PSM. Annealings were carried out either at fixed concentrations of additives using temperature gradients of 38-56° C. for N-WASP and 44-58° C. for the other targets, or at varying concentrations of additives using fixed temperatures of 41° C. for N-WASP, 50° C. for c-jun and PSM, and 54° C. for GTP.

Amplification products were analyzed by agarose gel electrophoresis on 0.8% agarose gels in which 20 ul reaction products were loaded with 4 ul loading buffer. Gels were stained with ethidium bromide, visualized on a UV transilluminator (Fisher), and documented by photography. Densitometric quantitation of amplification products was carried out using IMAGE SCANNER® and IMAGE MASTER® software from Amersham Pharmacia. Background correction was done using the software's rolling disc method.

First, polymerase activity assays were carried out in the absence of additives and in the presence of 1.0M 1,5-pentanediol and 0.7M 1,6-hexanediol at temperatures between 46 and 62° C. Next, polymerase activity was studied at 53° C. in the presence of concentration gradients of 1,5-pentanediol, 2-pyrrolidone, sulfolane and tetramethylene sulfoxide. The concentrations tested were: 1,5-pentanediol: 1.0, 1.3, 1.5, 2.25, 3.0 and 3.5M; 2-pyrrolidone: 1.25, 1.5, 2.0 and 3.9M; sulfolane: 1.0, 1.5, 2.0 and 2.75M, tetramethylene sulfoxide: 1.0, 1.5, 2.0 and 3.0M.

Results

The compounds utilized in the first phase (testing using 1.0M 1,5-pentanediol and 0.7M 1,6-hexanediol at temperatures between 46 and 62° C.) were chosen on the basis of the following rationale. The optimal additive for a low temperature PCR reaction is one that lowers the melting temperature of DNA as much as possible while minimally compromising polymerase activity. 1,5-Pentanediol and 1,6-hexanediol are both powerful DNA melting agents. In addition, it was found in the 62° C. activity studies that the rate of activity decline with concentration of 1,5-pentanediol was roughly equivalent to that of 1,2-butanediol, despite the fact that the former is a much stronger DNA denaturant. 1.0M 1,5-pentanediol and 0.7M 1,6-hexanediol are predicted to lower the $T_m$ of a 50% GC DNA by approximately the same amount: 19° C. While the inventors did not verify the linearity of cosolvent-induced $T_m$ depressions beyond concentrations yielding about a 10° C. depression, for the comparative purposes of this experiment it was assumed that the $\Delta T_m$s would be similar in these two cases.

FIG. 14 graphically depicts the measured variations of activity with temperature. Table lists the measured activity values, along with the magnitudes of the change in activity elicited by the additives at each temperature. The activity of the control decreases with temperature below 62° C. However, the activity in the presence of the additives increases between 62 and 53° C., reaching a maximum around 53° C. in both cases. A notable result is that activity in about a 5° C. temperature range—49° C.-53° C.—is in fact greater in the presence of both cosolvents than in their absence, possibly indicating that conformational loosening of the polymerase by the denaturant actually improves its function at these temperatures. Activation by 1,5-pentanediol exceeds 25%. At 48° C. and lower, the presence of the cosolvents deactivates the polymerase.

The temperature profile of Taq activity in the range 45-60° C., and its variation with cosolvent concentration, may provide an explanation for the often unpredictable variation in optimal annealing temperature. In most cases, a considerable amount of DNA synthesis probably occurred during the annealing step, especially since primer-templates are vary stable at the annealing temperature, compared to 72° C.; the extent of this synthesis at any given temperature is expected to vary from solvent to solvent due to the differential effects of solvents on polymerase activity. Significantly less amplification was observed when annealing temperatures below 47° C. were used, despite the greater stability of primer-template hybrids at low temperature; this may stem, in part, from the fact that the polymerase displays negligible activity at these temperatures.

With respect to the experiments studying polymerase activity at 53° C. in the presence of concentration gradients of 1,5-pentanediol, 2-pyrrolidone, sulfolane and tetramethylene sulfoxide, one goal of these studies was to approximate the upper end of the effective range of these compounds in PCR reactions using a 53° C. extension temperature. Accordingly, high concentrations were employed in the gradients. FIG. 15 displays the variation of activity with concentration in the case of each of these compounds. The results demonstrate that at high concentrations, 1,5-petanediol compromises polymerase activity to the least extent. Surprisingly, residual activity at 53° C. remains at even 3.5M (36.4%) 1,5-pentanediol. In the case of each compound, activity declines below control levels above 1.0M.

Primer melting temperatures ($T_m$s) were calculated using the Genosys oligo calculator program. The sequences of the primers were as follows.

```
N-WASP primer n1:
d(ATGAGCTCCGGCCAGCAGC),          (SEQ ID NO: 1)

primer n2:
d(TCAGTCTTCCCATTCATCATCATCATCCTC); (SEQ ID NO: 2)

c-jun primer j1:
d(ATGACTGCAAAGATGGAAACG);        (SEQ ID NO: 3)

primer j2:
d(TCAAAATGTTTGCAACTGCTG-CG);     (SEQ ID NO: 4)

PSM primer p1:
```

TABLE 5

Activity of Taq polymerase at selected temperatures below 62° C.: control, 1.0M 1,5-pentanediol and 0.7 M 1,6-hexanediol[1]

|  | 47° C. | 48° C. | 49° C. | 50° C. | 51° C. | 52° C. | 53° C. | 54° C. | 55° C. |
|---|---|---|---|---|---|---|---|---|---|
| Control | 0.33 | 0.41 | 0.49 | 0.50 | 0.53 | 0.51 | 0.57 | 0.61 | 0.70 |
| 1.0M 1,5-Pentanediol | 0.30 | 0.40 | 0.54 | 0.59 | 0.64 | 0.69 | 0.70 | 0.63 | 0.57 |
| Activation | −9% | −3% | +10% | +18% | +21% | +35% | +23% | +3% | −19% |
| 0.7M 1,6-Hexanediol | 0.24 | 0.36 | 0.57 | 0.60 | 0.60 | 0.64 | 0.64 | 0.60 | 0.51 |
| Activation | −27% | −12% | +16% | +20% | +13% | +25% | +12% | −2% | −27% |

[1]Activities normalized to activity of control at 62° C.

Example 4

Enhancement of Polynucleotide Amplification with Low Temperature Polymerase Activity Studies Investigations into the PCR enhancing capabilities of further lowering PCR extension and denaturation temperatures to temperatures lower than those utilized in Example 3 were carried out in Example 4 and demonstrated the superior effectiveness of the lower extension and denaturation temperatures in PCR enhancement.

Materials and Methods

Amplification reactions were carried out under the following general conditions. Those skilled in the art will appreciate, however, that to the extent that the conditions (set forth in this application) required for specific experiments described in this example were inconsistent with the following general conditions, limited exceptions to the following general conditions were made The general conditions were as follows: 10 Mm Tris-HCl (Ph 8.8), 50 Mm KCl, 1.5 Mm MgCl2, 0.01% (w/v) gelatin, 0.2 Um primers, 0.06 ng/ul template, 0.2 Mm each Dntp, 0.04 U/ul Taq polymerase. The templates used were bovine brain N-WASP cDNA (1518 bp), a 996 by segment of human myeloid leukocyte c-jun cDNA, a 511 by segment of human prostate-specific membrane antigen (PSM) cDNA, and bovine brain glycolipid transfer protein (GTP) cDNA (660 bp). cDNA synthesis was carried out using the FIRST-STRAND® RT-PCR kit from Stratagene on the respective mRNAs purchased from Clontech. All amplification reactions for gene were carried out using a single master batch of cDNA. Taq polymerase and dNTPs were obtained from Stratagene. Primers were obtained from Genosys.

```
                        -continued
d(AAACACTGCTGTGGTGGA);           (SEQ ID NO: 5)

primer p2:
d(TAGCTCAAC-AGAATCCAGGC);        (SEQ ID NO: 6)

GTP primer g1:
d(GAATTCGAAATGGCGCTGCTGCTGG);    (SEQ ID NO: 7)

Primer g2:
d(CTCGAGGTCCAGAGTACCCGCTGTG).    (SEQ ID NO: 8)
```

Calculated

Tms of the primers were as follows: n1-72.4° C., n2-70.7° C., j1-63.9° C., j2-70.8° C., p1-60.3° C., p2-61.9° C., g1-73.3° C., g2-74.4° C.

Additive chemicals were obtained from the following sources. N-methylformamide, N, N-dimethylformamide, acetamide, N-methylacetamide, N,N-dimethylacetamide and propionamide were purchased from Acros. 2-pyrrolidone, N-hydroxyethylpyrrolidone and N-methylpyrrolidone were obtained as free samples from BASF Corporation. Isobutyramide was purchased from Aldrich. Formamide was purchased from Gibco-BRL.

Polymerase chain reactions for the N-WASP gene were conducted on a ROBOCYCLER® Gradient 40 thermal cycler from Stratagene using 100 ul solutions in 600 ul thin-walled tubes. For expediency, amplification of c-jun, PSM and GTP was carried out in a ROBOCYCLER® Gradient 96 thermal cycler from Stratagene using 50 ul solutions in 200 ul thin-walled tubes. Prior to Taq polymerase addition, a hotstart protocol was carried out that consisted of an initial cycle of 95° C. for 5 minutes (11) to ensure complete first-strand separation, followed by a cycle of 54° C. for 5 minutes. Amplifications were run for 30 cycles. Denaturation was done for 1 minute at the minimum temperatures that yielded discernable amplification: 92° C. for N-WASP and 95° C. for c-jun, PSM and GTP. Extension was done at 72° C. for periods depending on target length: 2 minutes for N-WASP, 1.5 minutes for c-jun and GTP, and 1 minute for PSM. Annealings were carried out either at fixed concentrations of additives using temperature gradients of 38-56° C. for N-WASP and 44-58° C. for the other targets, or at varying concentrations of additives using fixed temperatures of 41° C. for N-WASP, 50° C. for c-jun and PSM, and 54° C. for GTP.

Amplification products were analyzed by agarose gel electrophoresis on 0.8% agarose gels in which 20 ul reaction products were loaded with 4 ul loading buffer. Gels were stained with ethidium bromide, visualized on a UV transilluminator (Fisher), and documented by photography. Densitometric quantitation of amplification products was carried out using IMAGE SCANNER® and IMAGE MASTER® software from Amersham Pharmacia. Background correction was done using the software's rolling disc method. 1,5-pentanediol was used exclusively because it was found to compromise polymerase activity the least at high concentrations at 53° C. GTP was used as the target because it has the lowest GC content of the three templates used. PCR reactions were carried out in the presence of 1.0 and 1.5M 1,5-pentanediol under the conditions of 85° C. denaturing and 53° C. extension, using a 50° C. annealing temperature. In addition, 1.5M and 2.0M 1,5-pentandediol were tested using an 80° C. denaturing temperature, with identical annealing and extension temperature. Finally, 2.0, 2.5, and 3.0M 1,5-pentanediol were tested in GTP amplification employing a 75° C. denaturation temperature.

PSM was also tested with 1.0 and 1.5M 1,5-pentanediol using a 85° C. denaturing/50° C. annealing/53° C. extension. The denaturation temperature was then lowered to 80° C., and 2.5M 1,5-pentanediol tested. Amplification of PSM using a 75° C. denaturing temperature was not attempted.

Results

With respect to the first set of tests (PCR reactions in the presence of 1.0 and 1.5M 1,5-pentanediol under the conditions of 85° C. denaturing and 53° C. extension, using a 50° C. annealing temperature with GTP as the target), strong amplification was found in both cases, suggesting that the denaturation temperature could be lowered further. Yields from these reactions are compared to the potencies achieved under standard PCR conditions in Table 6. With respect to the 1.5M and 2.0M 1,5-pentandediol tests using an 80° C. denaturing temperature, while 1.5M failed to produce any discernable amplification, 2.0M produced high yield (Table 6). The 2.0 and 2.5M reactions were unsuccessful, but 3.0M 1,5-pentanediol succeeded in producing amplification. FIG. 16 compares the results achieved in these low temperature amplifications of GTP with those obtained in the inventors' previous experiments using a 20° C. greater denaturation temperature of 95° C.

With respect to the PSM tests, 1.0M did not amplify the target sequence, but 1.5M was successful. Specificity and yield are compared to previous results in Table 6. Substantial amplification was also produced when the denaturation temperature was then lowered to 80° C., and 2.5M 1,5-pentanediol tested (Table 6). FIG. 16 compares these low temperature PCR results with those achieved previously under standard conditions.

These experiments establish that low temperature PCR is a viable concept. A preferred strategy, to summarize, is to lower both the extension and denaturation temperatures in concert. Lowering the extension temperature allows the use of particularly high concentrations of PCR-enhancing additives without significantly compromising the activity of the polymerase. Reducing the denaturation temperature permits these high concentrations to be used, at least in part because the thermostability of the enzyme does not become a limiting factor. Conveniently, using high additive concentrations permits the DNA template to melt at these lower denaturation temperatures.

TABLE 6

Results of pilot low temperature PCR experiments

| Cycling conditions[a] | 1,5-Pentanediol concentration | GTP Potency[b] | PSM Potency[c] | Specificity[d] |
|---|---|---|---|---|
| 85/50/53° C. | 1.0 M | 2.78 | 0.00 | NA |
|  | 1.5 M | 2.64 | 2.08 | 86% |
|  | 2.0 M |  |  |  |
| 80/50/53° C. | 1.5 M | 0.00 |  |  |
|  | 2.0 M | 2.69 |  |  |
|  | 2.5 M |  | 1.40 | 92% |
| 75/50/53° C. | 2.0 M | 0.00 |  |  |
|  | 2.5 M | 0.00 |  |  |
|  | 3.0 M | 0.53 |  |  |
| Comparative standards[e] |  |  |  |  |
| 95/55/72° C. | 0.3 M 1,5-Pentanediol | 1.00 |  |  |
| 95/50/72° C. | 0.8 M 1,3-Butanediol |  | 1.00 | 94% |

Control potency in all low temperature experiments was zero.
[a]Denaturation/annealing/extension temperatures.
[b]Normalized maximum densitometric volume of target band: 1,5-pentanediol (95/72° C.) = 1.
[c]Normalized maximum densitometric volume of target band: 1,3-butanediol (95/72° C.) = 1.
[d]Densitometric volume of target band as percent of total volume.
[e]Best results achieved under conventional conditions.

Various scientific articles, patents, and other publications are referred to throughout the present application. Each of these publications is herein incorporated by reference in its entirety.

The present invention may be embodied in other specific forms without departing from the spirit or essential attributes of the invention. Accordingly, reference should be made to the appended claims, rather than the foregoing specification, as indicating the scope of the invention.

What is claimed is:

1. A composition for performing a polynucleotide replication reaction, which comprises a buffer, one or more template polynucleotides, nucleotide triphosphates, one or more polymerase enzymes or fragments thereof, and at least one organic diol having the formula $C_nH_{2n+2}O_2$, wherein n is an integer with value equal to or greater than three but less than or equal to six, wherein when n=3, the diol is 1, 3 propanediol, when n=4 the diol is 1,2-butanediol or 1,3-butanediol, and when n=6, the diol is 1,6-hexanediol or 1,2-hexanediol or 2-methyl-2,4-pentanediol, wherein said organic diol is proportioned to the other ingredients in a ratio that provides an effective concentration range greater than 0.01 molar but less than 2.5 molar of said organic diol, and wherein said composition is functional to produce a detectable amount of product in a polynucleotide replication reaction at a denaturing temperature lower than 95° C. and an extension temperature lower than 72° C.

2. The composition of claim 1, wherein the at least one organic diol is 1,2-Butanediol.

3. The composition of claim 1, wherein the at least one organic diol is 1,3-Butanediol.

4. The composition of claim 1, wherein the at least one organic diol is a pentanediol.

5. The composition of claim 1, wherein the at least one organic diol is 1,6-Hexanediol.

6. A composition for performing a polynucleotide replication reaction, which comprises a buffer, one or more template polynucleotides, nucleotide triphosphates, one or more polymerase enzymes or fragments thereof, and at least one organic diol having the formula $C_nH_{2n+2}O_2$, wherein n is an integer with value equal to or greater than three but less than or equal to six, wherein when n=3, the diol is 1, 3 propanediol, when n=4 the diol is 1,2-butanediol or 1,3-butanediol, and when n=6, the diol is 1,6-hexanediol or 1,2-hexanediol or 2-methyl-2,4-pentanediol, wherein said organic diol is proportioned to the other ingredients in a ratio that provides an effective concentration range greater than 0.01 molar but less than 2.5 molar of said organic diol, and wherein said composition is functional to produce a detectable amount of product in a polynucleotide replication reaction and a polymerase chain reaction specificity of at least 80%.

7. The composition of claim 6, wherein the at least one organic diol is 1,3-propanediol.

8. The composition of claim 6, wherein the at least one organic dial is 1,2-butanediol.

9. The composition of claim 6, wherein the at least one organic diol is 1,3-butanediol.

10. The composition of claim 6, wherein the at least one organic diol is 1,2-pentanediol.

11. The composition of claim 6, wherein the at least one organic diol is 2,4-pentanediol.

12. The composition of claim 6, wherein the at least one organic diol is 1,5-pentanediol.

13. The composition of claim 6, further comprising at least one organic diol that is cis-1,2-cyclopentanediol.

14. The composition of claim 6, wherein the at least one organic diol is 1,2-hexanediol.

15. The composition of claim 6, wherein the at least one organic diol is 1,6-hexanediol.

16. The composition of claim 6, wherein the at least one organic diol is 2-methyl-2,4-pentanediol.

17. A method for enhancing a polynucleotide amplification reaction, comprising adding to a polynucleotide amplification reaction mixture a low molecular weight diol in an amount effective to enhance the polynucleotide amplification, wherein said diol is an organic diol the formula $C_nH_{2n+2}O_2$, wherein n is an integer with value equal to or greater than three but less than or equal to six, wherein when n=3, the diol is 1, 3 propanediol and when n=4 the diol is 1,2-butanediol or 1,3-butanediol, and when n=6, the dial is 1,6-hexanediol or 1,2-hexanediol or 2-methyl-2,4-pentanediol, and wherein said organic diol is proportioned to the other ingredients in a ratio that provides an effective concentration range greater than 0.01 molar but less than 2.5 molar of said organic diol.

* * * * *

UNITED STATES PATENT AND TRADEMARK OFFICE
CERTIFICATE OF CORRECTION

| | | |
|---|---|---|
| PATENT NO. | : 7,772,383 B2 | Page 1 of 1 |
| APPLICATION NO. | : 10/792404 | |
| DATED | : August 10, 2010 | |
| INVENTOR(S) | : Chakrabarti et al. | |

It is certified that error appears in the above-identified patent and that said Letters Patent is hereby corrected as shown below:

Title page;

The Related U.S. Application Data should read:

--(63)  Continuation-in-part of application No. 10/056,917, filed on Jan. 25, 2002, now Pat. No. 6,949,368.--

Signed and Sealed this

Twenty-third Day of November, 2010

David J. Kappos
*Director of the United States Patent and Trademark Office*